(12) United States Patent
Dalton et al.

(10) Patent No.: US 9,072,881 B2
(45) Date of Patent: Jul. 7, 2015

(54) VASCULAR ACCESS PORT

(76) Inventors: Michael J. Dalton, Evanston, IL (US);
Jordan M. Dalton, Chicago, IL (US);
Natan A. Pheil, Chicago, IL (US)

(*) Notice: Subject to any disclaimer, the term of this patent is extended or adjusted under 35 U.S.C. 154(b) by 248 days.

(21) Appl. No.: 13/410,298

(22) Filed: Mar. 2, 2012

(65) Prior Publication Data

US 2013/0066282 A1    Mar. 14, 2013

Related U.S. Application Data

(60) Provisional application No. 61/454,526, filed on Mar. 19, 2011.

(51) Int. Cl.
*A61M 5/14* (2006.01)
*A61M 39/02* (2006.01)

(52) U.S. Cl.
CPC ..... *A61M 39/0208* (2013.01); *A61M 2039/022* (2013.01); *A61M 2206/20* (2013.01)

(58) Field of Classification Search
CPC ........................ A61M 39/02; A61M 39/0208
USPC ..................................................... 604/288.01
See application file for complete search history.

(56) References Cited

U.S. PATENT DOCUMENTS

| | | | |
|---|---|---|---|
| 5,562,617 A * | 10/1996 | Finch et al. | 604/288.02 |
| 5,647,855 A * | 7/1997 | Trooskin | 604/175 |
| 6,997,914 B2 * | 2/2006 | Smith et al. | 604/288.04 |
| 2006/0184142 A1 * | 8/2006 | Schon et al. | 604/288.02 |
| 2007/0073250 A1 * | 3/2007 | Schneiter | 604/288.01 |
| 2008/0140025 A1 * | 6/2008 | Sheetz et al. | 604/288.02 |
| 2009/0099538 A1 * | 4/2009 | Paganon | 604/288.02 |

* cited by examiner

*Primary Examiner* — Laura Bouchelle
(74) *Attorney, Agent, or Firm* — Soula Skokos; Skokos Law Group LLC

(57) ABSTRACT

An implantable infusion port comprising a non planar septum, a fluid reservoir of a substantially spherical shape, inlet means to access the reservoir, and optimized outlet means from the reservoir. The present invention provides for a reservoir that precludes angular junctions between portions of the reservoir which can lead to eddies, countercurrents, and stagnation, thereby creating a more laminar and efficient flow pattern within the reservoir.

46 Claims, 32 Drawing Sheets

SECTION A-A

SCALE 6:1

TOP VIEW

SCALE 6:1

TOP VIEW - NO SEPTUM

SCALE 6:1

BOTTOM VIEW

SCALE 6:1

ISOMETRIC VIEW

RADIUSED SEPTUM PRIOR TO ASSEMBLY

ISOMETRIC EXPLODED VIEW

FRONT VIEW

TOP VIEW

SCALE 6:1

ISOMETRIC VIEW

SCALE 6:1

FRONT VIEW

TOP VIEW

SCALE 6:1

ISOMETRIC VIEW

SCALE 6:1

FRONT VIEW

SECTION C-C

SCALE 6:1

RIGHT VIEW

SECTION D-D

SCALE 6:1

TOP VIEW - NO SEPTUM

SCALE 6:1

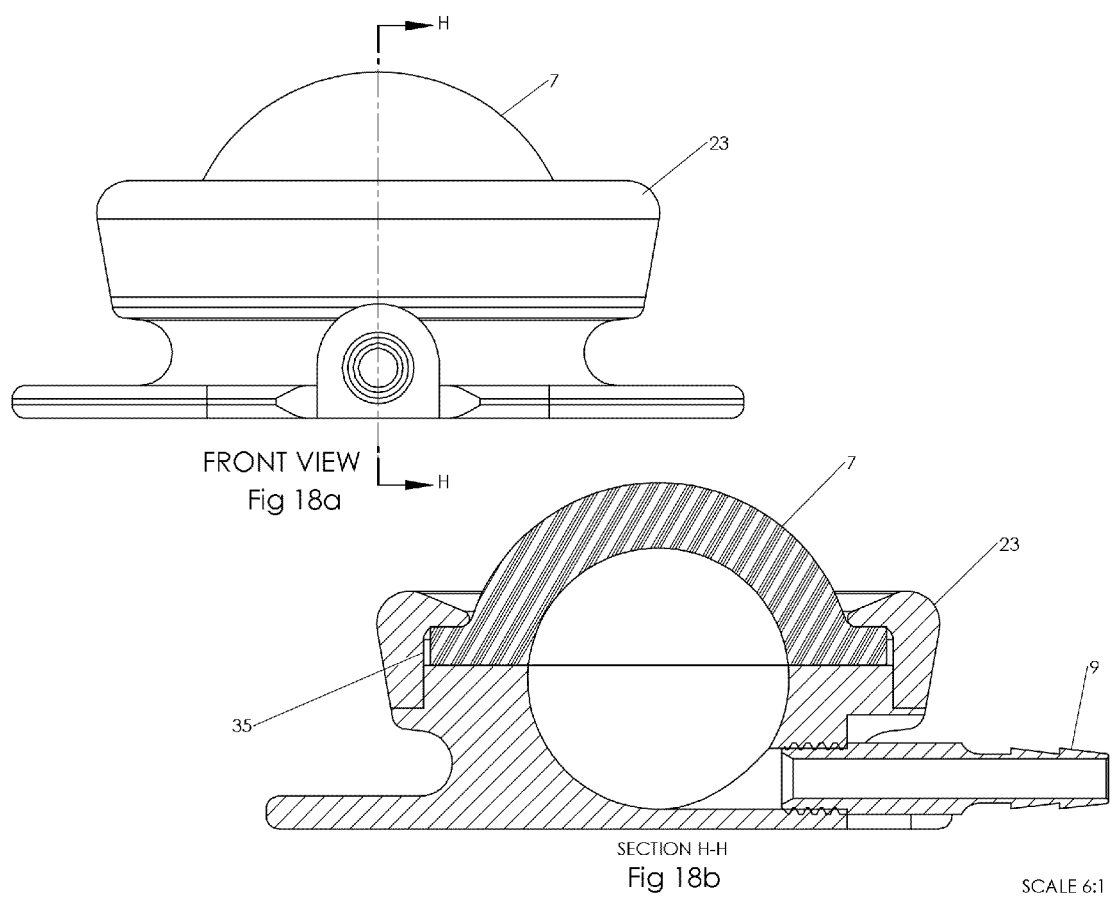

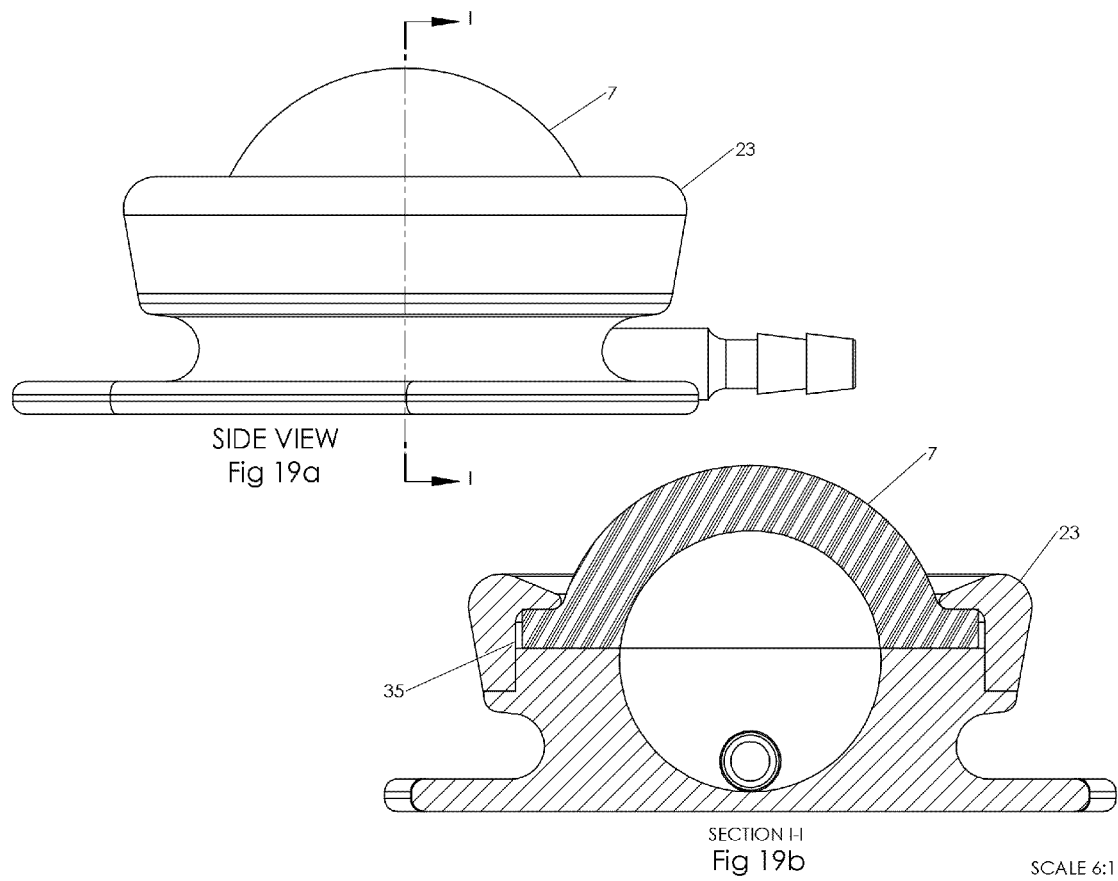

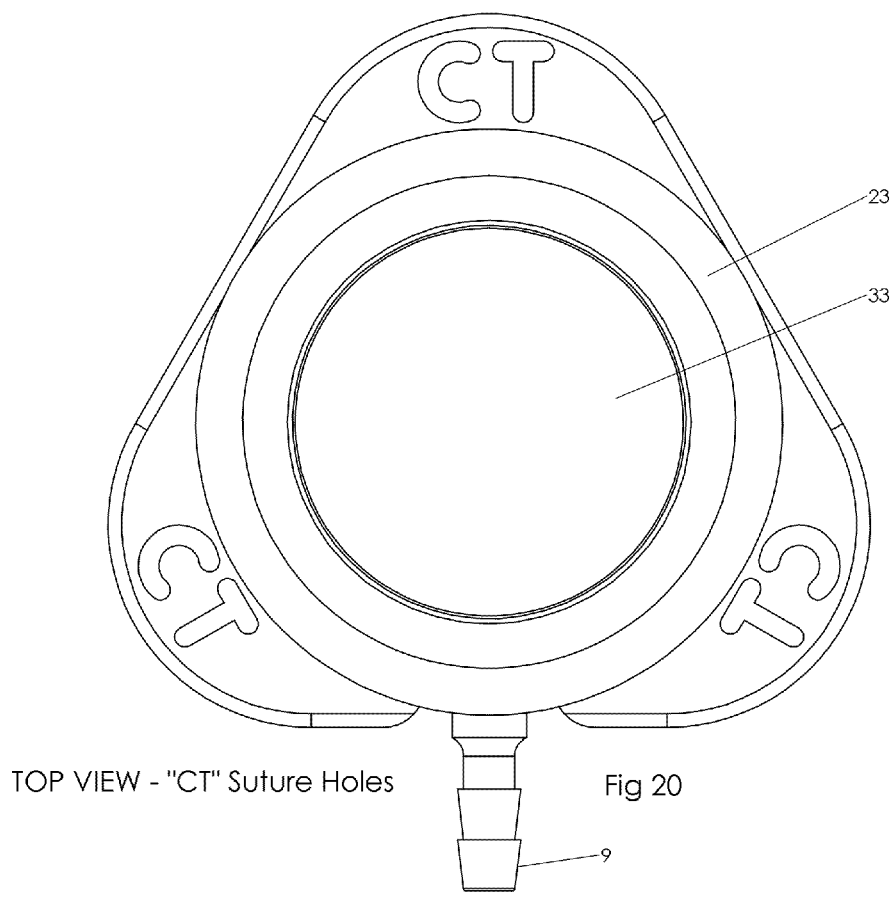
TOP VIEW - "CT" Suture Holes    Fig 20

TOP VIEW - 2 "CT" and 1 Regular Suture Holes

TOP VIEW - 1 "CT" and 2 Regular Suture Holes

TOP VIEW - Regular Suture Holes

SCALE 2:1

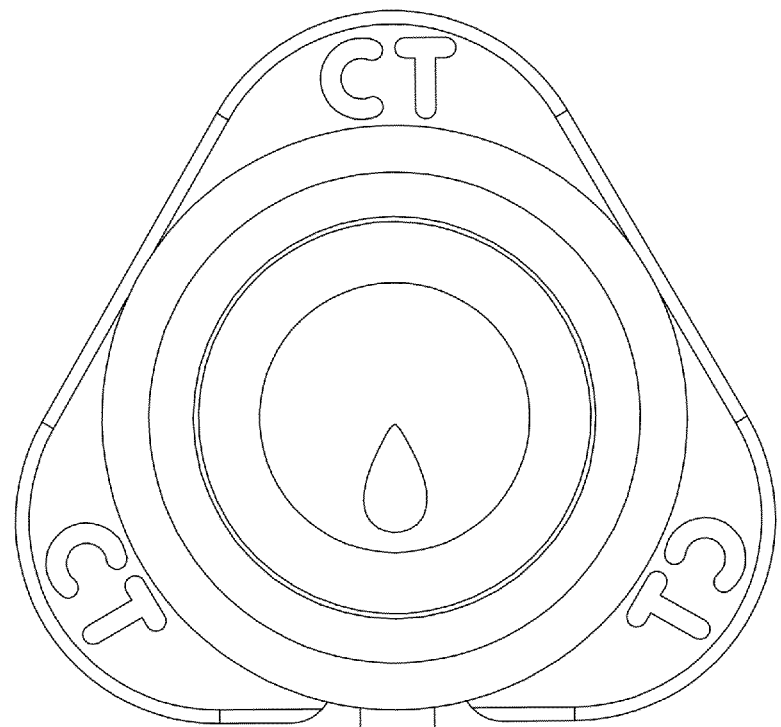
TOP VIEW - No Septum     Fig 22
SCALE 6:1

ISOMETRIC VIEW

SCALE 6:1

ISOMETRIC VIEW - Exploded

Septum - As Molded (non-Sealing)

Septum - Reversed (Self-Sealing)

SCALE 6:1

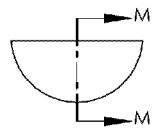
Septum - Molded (non-Sealing)
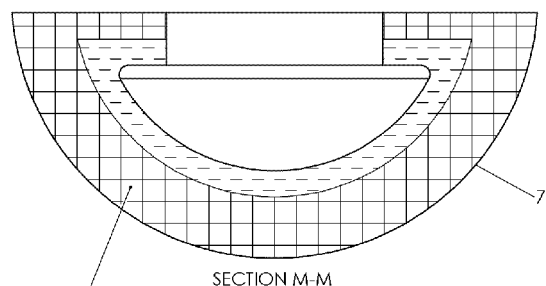
SECTION M-M
SCALE 8 : 1
Uniform molecular structure —> non-sealing
Fig 27a
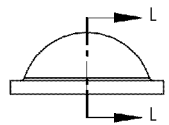
Septum - Reversed (Self-Sealing)
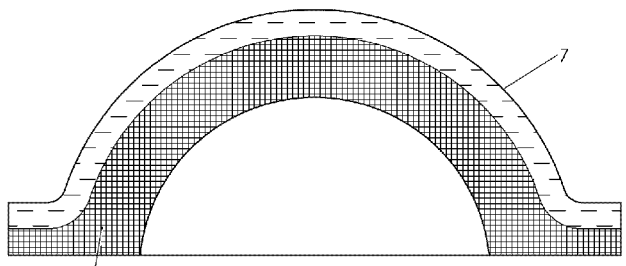
SECTION L-L
SCALE 8 : 1
Compressed (reversed) molecular structure —> sealing
Fig 27b
SCALE 2:1

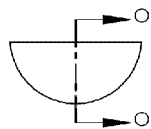
Septum - Molded (non-Sealing)
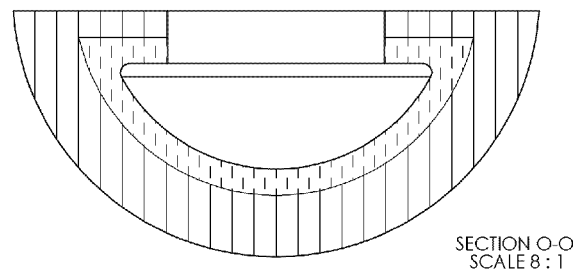
Non-competing Forces = Non-sealing
Fig 28a
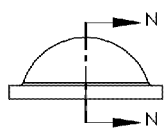
Septum - Reversed (Self-Sealing)
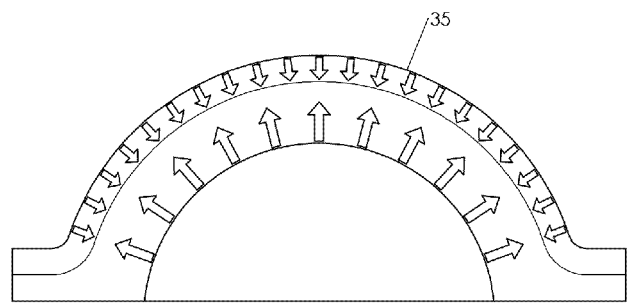
Competing Forces = Sealing
Fig 28b
SCALE 2:1

Chart 1 – Conductivity vs. Clearance Volume, 5 mL/min

Chart 2 – Conductivity vs. Clearance Volume, 10 mL/min

Chart 3 – Conductivity vs. Clearance Volume, 20 mL/min

VASCULAR ACCESS PORT

CROSS REFERENCE

This application claims priority from U.S. Provisional Patent Application Ser. No. 61/454,526, filed Mar. 19, 2011 of the same title.

FIELD OF THE INVENTION

The present invention relates to implantable medical devices for subcutaneous implantation and which can be accessed through the skin, such as with a needle coupled to a syringe for delivery of therapeutic preparations into the vascular structure of the patient. More particularly, this invention relates to access ports having a modified reservoir and unique radiused septum in addition to a unique overall shape.

BACKGROUND OF THE INVENTION

The use of an implantable infusion port for the delivery of drugs is well known in the art. Current devices typically comprise a needle-impenetrable cylindrical reservoir connected to a catheter for placement into an appropriate vessel that is accessible from the exterior through a generally planar septum that covers the reservoir. The purpose of an implantable infusion port is to provide the user with means for frequent blood sampling, delivery of medications, nutrients, and blood products, and imaging solutions to the patient's blood stream or desired location within the patient's body. The implantable infusion port is accessed by use of a special needle that may be inserted through the patient's skin and through the penetrable septum to access the reservoir. Current devices generally possess a cylindrical reservoir to be accessed by the user. A standard port contains a reservoir with straight walls and generally flat bottom base and an outlet catheter at the junction of the reservoir and base. The use of a cylindrical reservoir with straight walls and a flat bottom, however, creates "corners" or angular junctions, specifically where the bottom wall of the reservoir meets the continuous side wall. The design of a cylindrical reservoir will necessarily require the side wall of the reservoir to meet the bottom wall at approximately a ninety degree angle. One example of a cylindrical reservoir in an implantable infusion port is disclosed in U.S. Pat. No. 4,673,394. Although cylindrically shaped reservoirs are commonly used in such implantable devices, the angular junctions in such reservoirs may pose significant health risks to the patient over time. As will be discussed further below, a major issue with implantable infusion ports is the accumulation of debris and residue over time that may eventually lead to an infection for the patient and the occlusion of the device. With current port technology, such angular junctions are present not only where the bottom wall of the reservoir meets the continuous side wall, but also where the continuous side wall meets the planar septum covering the reservoir. The use of a generally planar septum to cover the cylindrical reservoir creates an additional angular junction where the side wall of reservoir meets the planar septum. The current technology therefore teaches a 90 degree angled junction at both the perimeter of the bottom wall and the top edge of the side wall where the side wall meets the bottom surface of the septum, thereby creating a large area in which debris and residue can accumulate and cause complications for the user. A significant drawback of the current technology is that the design of the reservoir and septum provides ample opportunity for debris and residue to accumulate which may compromise the safety of the patient over time.

Although the prior art, such as U.S. Pat. No. 5,713,859, may suggest a reservoir base with a slight radius or chamfer at the bottom of the reservoir to reduce the potential for debris build-up, such a design does not solve the problem of debris build up. A chamfered or rounded base still poses an angular junction where the continuous side wall meets the planar septum covering the reservoir.

Once implanted, infusion ports may remain in the body for periods of months to years. Due to such lengthy periods, the reservoir of the port can become contaminated and begin to harbor agents of disease. This can lead to problems, such as infection within the fleshy pocket beneath the skin occupied by the infusion port and blood borne infection traveling throughout the body. Such infection can require extensive therapy which may include removal of the infusion port. Currently, there is no practical way to monitor the effectiveness of the cleansing practice while the infusion port is implanted in the body and hidden under the skin.

As a result of investigating the fate of various discarded infusion ports recovered after being implanted and employed in the manner described above for various periods of time, it has been discovered that in almost every case the reservoir contained a deposit of clotted blood and/or drug residue. When allowed to stagnate, blood will form a cohesive mass, or coagulate, which is the body's natural mechanism to protect itself against excessive bleeding from a wound. According to principles of fluid dynamics, stagnation occurs in corners or areas where turbulence occurs. This issue with current ports, therefore, is that the presence of angular junctions and corners in the port reservoir can allow the blood to stagnate, and, once the blood coagulates, it can become very difficult to flush out. Sophisticated lysing drugs would then become necessary to dissolve such residue.

In many cases the residue, when cultured, exhibits the presence of bacterial and fungal organisms, such as *Staphylococcus aureus, Staphylococcus epidermidis*, and fungus of the genus *Candida*. In an attempt to clear the debris which can accumulate, especially at the angular junctions within the reservoir, thrombolytic agents have been developed. The use of such sophisticated materials to remedy an inherent infusion port design problem is expensive and puts the patient at risk of both infection and adverse reactions from the lysing agent.

What is required, therefore, is an implantable vascular access port that overcomes the drawbacks of the current technology by having a novel reservoir and septum design that attempts to eliminate angular junctions and improve flow patterns within the reservoir.

In addition to eliminating these angular junctions and improving flow patterns, another aim is to reduce the reservoir volume, or "dead space". Due to a cylindrically shaped reservoir, current port devices possess a necessarily larger reservoir, and, therefore, a larger "dead space." The distance between the bottom surface of a septum and the bottom of a reservoir base is a fixed number. This volume of the cylinder is termed the "dead space." It is believed that the larger the dead space, the greater the potential for residue and debris to accumulate. It is desirable, therefore, to have an implantable vascular access port causing minimal dead space while still maximizing the needle penetrable surface area of the septum.

Another drawback of current port devices is that the common method among practitioners is to introduce the needle perpendicular to the top surface of the septum. The rational for such method is that when introducing the needle into the septum, the entire tip of the needle needs to not only penetrate the septum but needs to pass below the bottom surface of the septum in order for the fluid being inserted or infused to flow freely from the tip of the needle. With current port devices having a planar septum, the point of the needle will in most instances be introduced perpendicularly to the planar surface of the septum, and, after the needle tip has been introduced, the needle tip will come into contact perpendicularly with the planar surface of the bottom of the reservoir as well. Therefore, in current devices having a planar septum, the plane of the septum and the plane of the bottom surface of the reservoir must be parallel. The obstacle with such a design is that at some points in the needle accessible area of the septum, such as the periphery of the septum, the needle tip may not have clearance through the bottom of the septum and therefore not able to freely infuse or introduce fluids. What is desired, then, is an implantable vascular access port wherein the user is capable of introducing a needle perpendicular to the surface of a septum but wherein the plane of the septum is not necessarily parallel to the bottom of the reservoir.

Current vascular ports are also designed to have an outlet opening connected to an outlet tube, such as a catheter, to allow the flow of fluids from the reservoir to such an outlet tube. The issue present with current vascular access ports is that the outlet opening in the reservoir does not aid in the flow pattern of the fluid flowing from the reservoir to the outlet tube. This is because the outlet opening and surrounding structure are ninety degrees relative to the side wall of the reservoir. Such geometry of the opening disrupts flow into the outlet tube. The present invention is directed at overcoming the drawbacks of the current technology by having a novel outlet opening design to aid in the flow from the reservoir to the outlet tube.

SUMMARY OF THE INVENTION

It is an object of this invention to reduce or prevent the accumulation of undesirable residues in infusion ports. It is another objective to alleviate the residue deposition problem without disrupting currently accepted clinical protocols requiring that infusion ports be routinely flushed with aqueous saline between injections of medication or withdrawals of body fluid. It is another objective to improve the flow pattern of fluids from the reservoir to the outlet tube. It is another objective to attain these ends by means of simple structural modification of the infusion ports of the prior art. It is another objective of this invention to create a device that is accessed by the caregiver in the same manner as is currently used. Other objectives will become apparent hereinafter.

Consequently, this invention provides an implantable infusion port which comprises a non planar septum, a fluid reservoir of a substantially spherical shape, inlet means to access the reservoir, and optimized outlet means from the reservoir. The present invention provides for a reservoir that precludes angular junctions between portions of the reservoir which can lead to eddies, countercurrents, and stagnation, thereby creating a more laminar and efficient flow pattern within the reservoir. The novel design of the reservoir permits efficient cleaning of the reservoir and other components of the infusion port.

It is further an object of the present invention to provide a physiologically beneficial shaped septum that may aid in alleviating the erosion issue present in current port technology. All of the prior art teaches a planar or flat septum that is secured to the reservoir base by use of a retainer ring or septum ring. The planar or flat septum and retainer ring creates a round harsh footprint pushing upward out of the patient's skin. This can lead to erosion problems. In a preferred embodiment of the present invention, the non planar septum is radiused to follow the natural contour of the skin. In the present invention, the perimeter of the septum retainer and septum fall away from the center point of the septum thereby creating a smaller, gentler footprint on the skin surface. The septum retainer, or ring encircling the septum, is used to secure the septum in place and provides the caregiver with a feel similar to conventional ports.

It is further an objective of this invention to create a more efficient flushing infusion port. The non-planar septum and spherical reservoir provide a smaller volume reservoir thereby reducing the residual volume in the port and creating a more efficient cleaning and flushing port. The reduction in the volume of the reservoir can be quite significant because such area is where sludge, drug residue, and blood products remain and pose infection risks and problems with the function of the port.

It is another objective of the invention to provide a septum that when a user advances a septum puncturing needle into the improved port, the septum puncturing needle passes perpendicular to the surface of the septum that the nurse palpates.

It is further an object of the present invention to provide more efficiently shaped outlet means to improve the flow pattern and flushing efficiency of the reservoir. The present invention provides outlet means that may be directed along the plane of the bottom wall of the reservoir to create a more efficient flow pattern. To further improve the flow pattern, the structure surrounding the outlet opening may be beveled, chamfered or rounded to improve the flow of fluids from the reservoir to the outlet tube.

BRIEF DESCRIPTION OF THE DRAWINGS

FIG. 18a is front view of a spherical reservoir vascular access port designed in accordance with an embodiment of the present invention;

FIG. 18b is a cross sectional view of a spherical reservoir vascular access port designed in accordance with an embodiment of the present invention;

FIG. 19a is a side right view of a spherical reservoir vascular access port designed in accordance with an embodiment of the present invention;

FIG. 19b is a cross sectional view of a spherical reservoir vascular access port designed in accordance with an embodiment of the present invention;

FIG. 20 is a top view of a spherical reservoir vascular access port designed in accordance with an embodiment of the present invention wherein the suture holes are cut outs of the letters "CT";

FIG. 22 is a top view of a spherical reservoir vascular access port with the septum removed designed in accordance with an embodiment of the present invention wherein the suture holes are combination of suture holes and cut outs of the letters "CT";

FIG. 27a is a cross sectional view of the septum of the present invention designed in accordance with an embodiment of the present invention wherein the septum is constructed to be self-sealing.

FIG. 27b is a cross sectional view of the septum of the present invention designed in accordance with an embodiment of the present invention wherein the septum is constructed to be self sealing and the septum inverted.

FIG. 28a is a cross sectional view of the septum of the present invention designed in accordance with an embodiment of the present invention wherein the septum is constructed to be self sealing.

FIG. 28b is a cross sectional view of the septum of the present invention designed in accordance with an embodiment of the present invention wherein the septum is constructed to be self sealing and inverted.

DETAILED DESCRIPTION OF THE DRAWINGS

Figure 1:
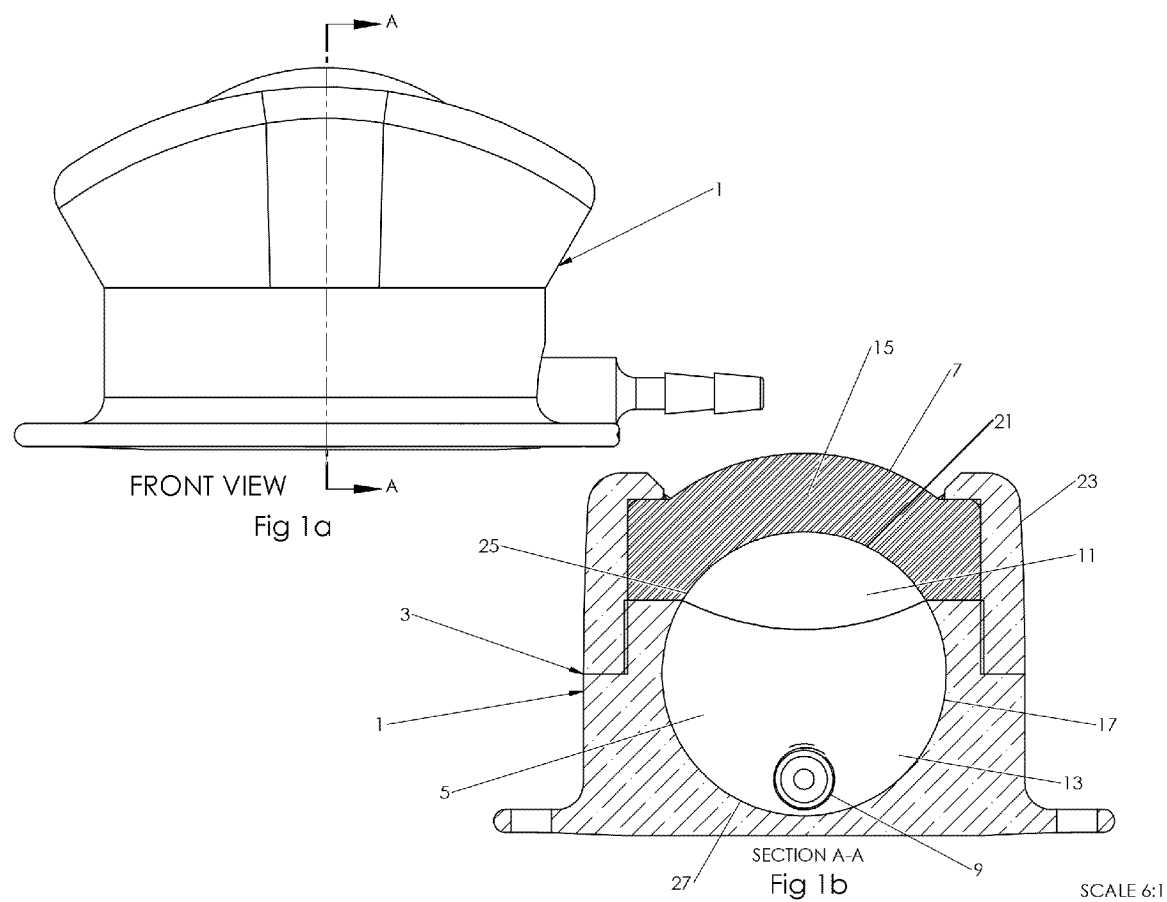
FIG. 1a is front view of a spherical reservoir vascular access port designed in accordance with an embodiment of the present invention.
FIG. 1b is a cross sectional view of a spherical reservoir vascular access port designed in accordance with an embodiment of the present invention.
Figure 2:
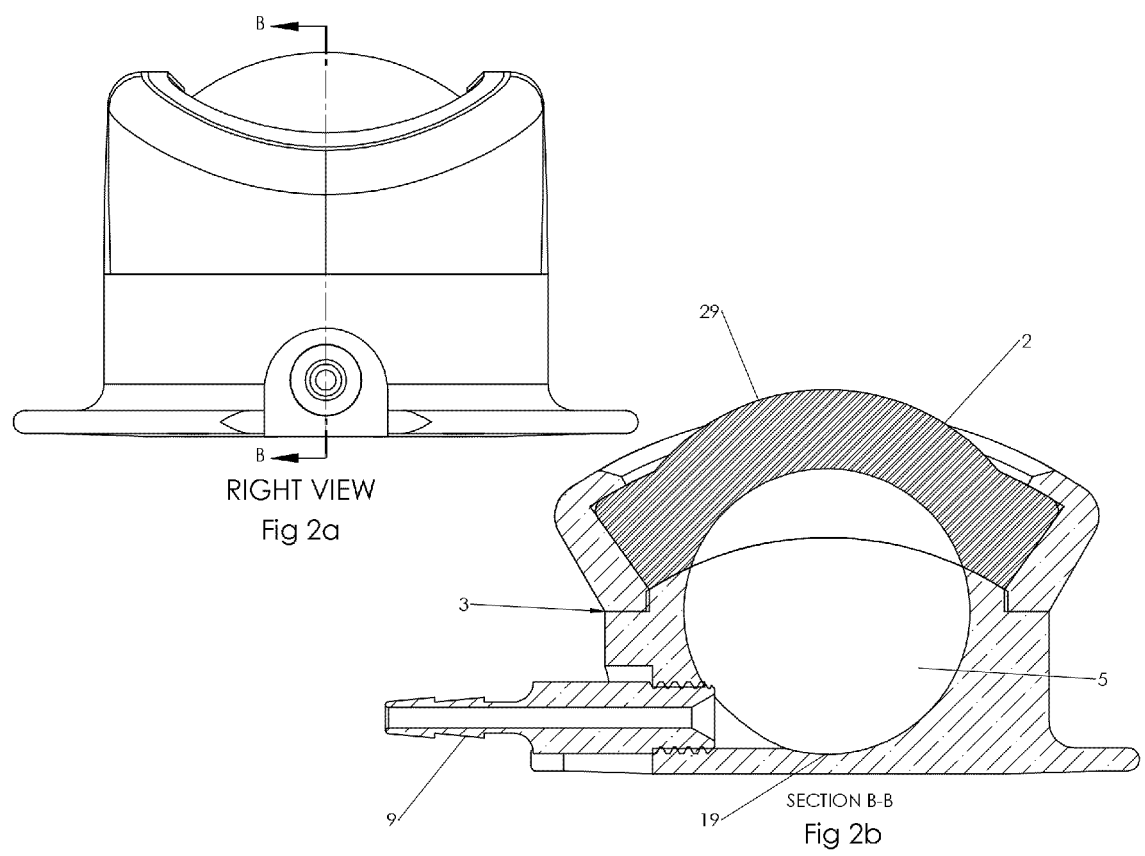
FIG. 2a is a side right view of a spherical reservoir vascular access port designed in accordance with an embodiment of the present invention.
FIG. 2b is a cross sectional view of a spherical reservoir vascular access port designed in accordance with an embodiment of the present invention.

The present invention is shown generally as 1 in FIG. 1a. As shown in FIGS. 1b and 2b, the present invention is comprised of a needle impenetrable housing 3 enclosing a fluid reservoir 5 of a substantially spherical shape, inlet means to access the reservoir in the form of a non-planar elastomeric septum 7, and outlet means from the reservoir 9. The novel shape of the reservoir 5 of the present invention addresses the shortcomings of current devices having "corners" where the side wall of the reservoir meets the bottom wall of the reservoir and also where the top edge of the side wall meets the septum. It is well known that debris can accumulate at such corners and angular junctions. To solve this problem, the present invention provides a reservoir 5 that is substantially fully spherical in shape thereby precluding any angular junctions between the reservoir and the septum. While there are infusion ports that have reservoirs having rounded edges, there currently does not exist a port having a substantially spherically shaped reservoir.

The shape of the reservoir 5 is achieved by the combination of the novel septum design and the novel shape of the reservoir. According to principles of fluid mechanics, the efficiency of fluid mixing in a container is lower near the walls of the container and especially in any corners where elements of the container wall join together angularly. The more acute the angle, the lower the mixing efficiency. Laminar flow along the walls of the conduit or reservoir enhances the cleansing or clearing of the reservoir. Laminar flow occurs in areas of smooth wall transitions only. As shown in FIGS. 1b and 2b, the needle impenetrable housing 3 of the present invention provides a semi-spherical reservoir 5 and, consequently, there are no angular junctions between portions of the reservoir 5. The smooth transitions between the top and bottom portions of the reservoir, 11 and 13, enhance the flushing efficiency and fluid dynamics. This principle applies to both flushing and cleansing of the reservoir of a port. After each infusion or blood withdrawal, the reservoir must be flushed of the debris including but not limited to blood, chemotherapeutic agents, or drugs.

The novel septum design of the present invention further enhances the shape of the reservoir 5. The septum designs of the prior art teaches that the septum is planar and lies in a plane parallel to the aperture of a reservoir cap. As shown in FIGS. 1b and 2b, the septum 7 of the present invention, however, forms a convex configuration wherein the center of the septum 15 bulges outward in relation to the periphery of the septum. The convex configuration of the septum exterior to the reservoir 5 allows the user to easily palpate the septum area. As shown in FIGS. 1b and 2b, the configuration of the septum 7 further provides for a concave inner surface in relation to the side wall 17 of the reservoir. By having the septum 7 form a concave inner surface, the reservoir 5 provides a smooth continuous walled chamber and forms a reservoir 5 that resembles a truly spherical shape. The concave design of the floor 19 is opposite the concave design of the septum which describes the spherical shape of the chamber.

Figure 7:
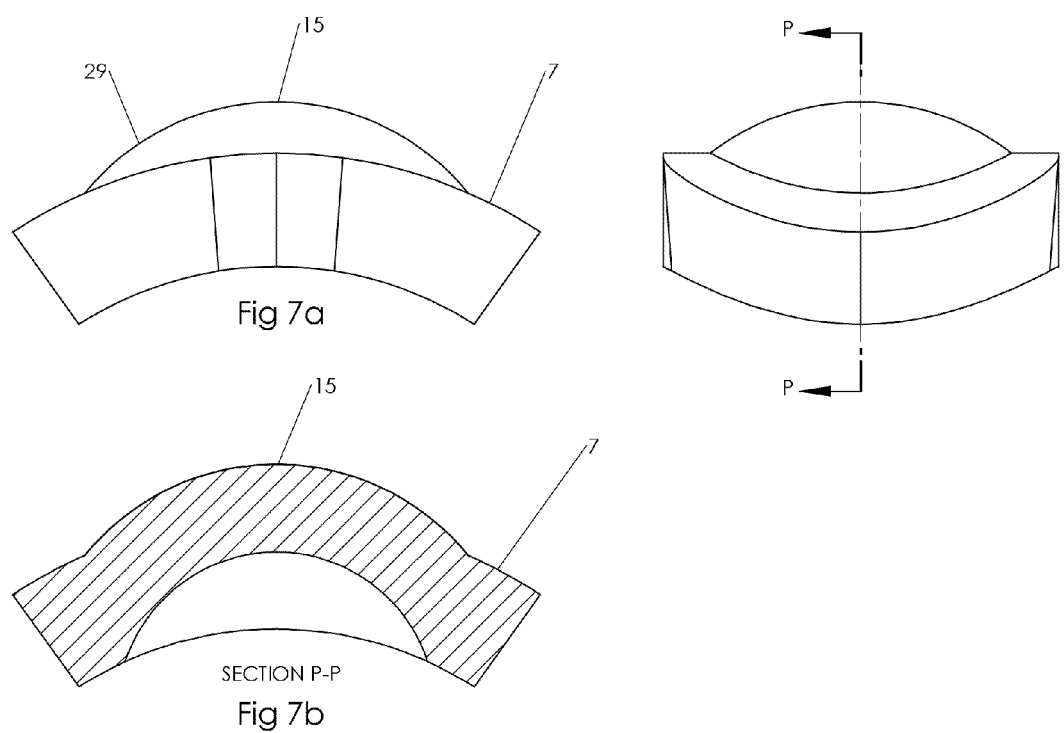
FIG. 7a is a front view of the septum of the present invention designed in accordance with an embodiment of the present invention wherein the septum is radiused.
FIG. 7b is a cross sectional view of the septum of the present invention designed in accordance with an embodiment of the present invention wherein the septum is radiused.
Figure 8:
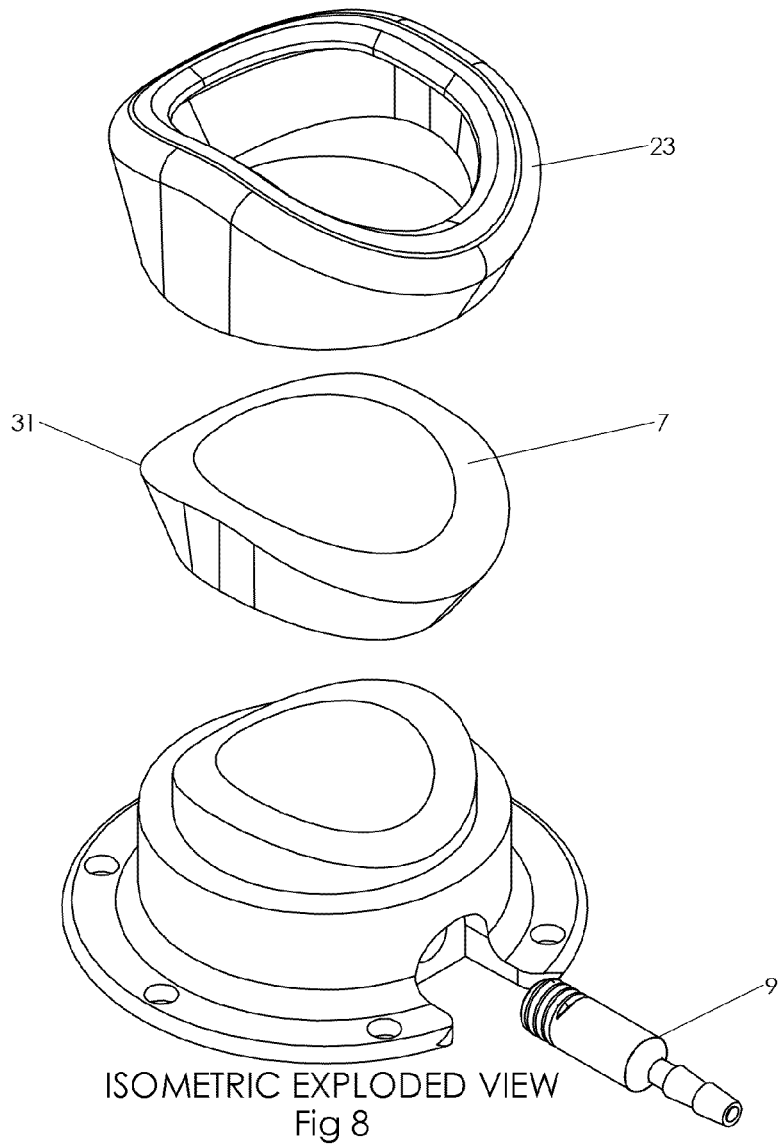
FIG. 8 is an exploded isometric view of a spherical reservoir vascular access port designed in accordance with an embodiment of the present invention.

As shown in FIG. 1b, the bottom portion of the septum forms a concave inner surface that, when assembled in the vascular access port, forms the top portion of the spherically shaped reservoir. In standard ports, when the septum retainer ring is secured to the reservoir base, the compression of the septum causes the septum to bulge both upward toward the exterior of the vascular access port and downward towards the bottom of the reservoir. The bulging of the septum within the reservoir results in the creation of tight corners in which residue and debris can accumulate. In the present invention, as is shown in FIG. 7b, the septum 7, prior to its assembly into the vascular access port 1, is non-planar and is shaped to have a concave bottom surface. As shown in FIGS. 1b and 2b, when the vascular access port 1 is assembled, the concave bottom surface 21 of the septum provides a rounded top to the reservoir 5 thereby allowing the reservoir 5 to become spherical in shape. In a preferred embodiment, the pre-assembled septum may be slightly larger in diameter that the septum retainer ring 23. By having a concave bottom surface 21 and having a slightly larger diameter than the septum retainer ring 23 into which it fits, the septum 7, specifically the center 15 of the septum, bulges upward toward the exterior of the vascular access port 1 when the vascular access port 1 is assembled, and the septum 7 is compressed. The upward bulge in the septum 7, the concave shape 21 of the bottom surface of the pre-assembled septum, and the compression forces on the septum 7 at its outer periphery 25 when assembled aid in the formation of a spherically shaped reservoir 5. By having a diameter slightly larger than the retainer ring 23, the septum 7 is compressed along the horizontal plane towards the center 15 of the septum thereby causing the center 15 of the septum to bulge upward toward the exterior of the vascular access port 1 and forming the top portion of the spherical reservoir 5. The concave bottom surface 21 of the pre-assembled septum 7 further enhances this bulging effect since the compression of the septum 7 upon assembly causes the concave shape of the bottom surface 21 of the septum 7 to become hemispherical in shape. By having the portion of the septum 7 exposed to the reservoir 5 become hemispherical in shape, the reservoir 5 truly becomes a spherical chamber precluding any angular junctions or corners in which debris and/or residue may accumulate.

Another benefit of the present invention is that it provides a physiologically beneficial shaped septum that may aid in alleviating the erosion issue present in current port technology. The prior art teaches a planar, or flat, septum that is secured to the reservoir base by use of a retainer ring or septum ring. The planar septum and retainer ring creates a round, harsh footprint pushing upward out of the patient's skin, leading to erosion problems. In a preferred embodiment of the present invention, as shown in FIGS. 6, 7a, 7b, and 8, the non-planar septum 7 and septum retainer 23 may be radiused to follow the natural contour of the skin. In the present invention, the perimeter of the septum 7 and septum retainer 23 fall away from the center point of the septum 15, thereby creating a smaller, gentler footprint on the skin surface.

Another benefit of the present invention is that the non-planar septum 7 provides a diffuse area for a nurse or user to penetrate the septum 7. In practice, a nurse or caregiver palpates the septum area through the patient's skin and advances the septum-penetrating needle perpendicular to the surface of palpated septum. With standard ports, the use of a generally planar septum limits the concentration of needle puncture sites to the center of the septum area. The objective of the non planar septum 7 of the present invention is twofold: 1) to create a diffused area for needle penetration and to enhance the dispersion of needle puncture sites to prevent coring of the septum 7, premature failure of the septum 7, and/or leaking of the septum 7 due to too many punctures in the same spot, and 2) where the needle is advanced perpendicular to the septum 7, the needle point will contact a surface that is perpendicular to the line of the advancing needle.

Another advantage of the non-planar septum 7 is that when a user advances the needle into the port, it passes perpendicular to the surface of the septum 7 that the nurse palpates. With an elongated, radiused, and non-planar septum 7, the needle punctures the septum 7 at different points while allowing the needle to bottom out at different locations along the reservoir bottom wall surface 27. This randomization of the needle flush point, or the position where the flush solution flows out of the needle, creates an improved flow pattern in the reservoir 5, thus cleaning various areas of the port 1 at each use. Such increased randomization of the needle flush point is not present with standard ports. When the needle is placed in the same center spot for every septum puncture, a specific flow pattern is developed within the reservoir. This creates the residual sludge build-up in the corners or in non-flushed areas, thereby posing an increased risk of infection.

Figure 3:
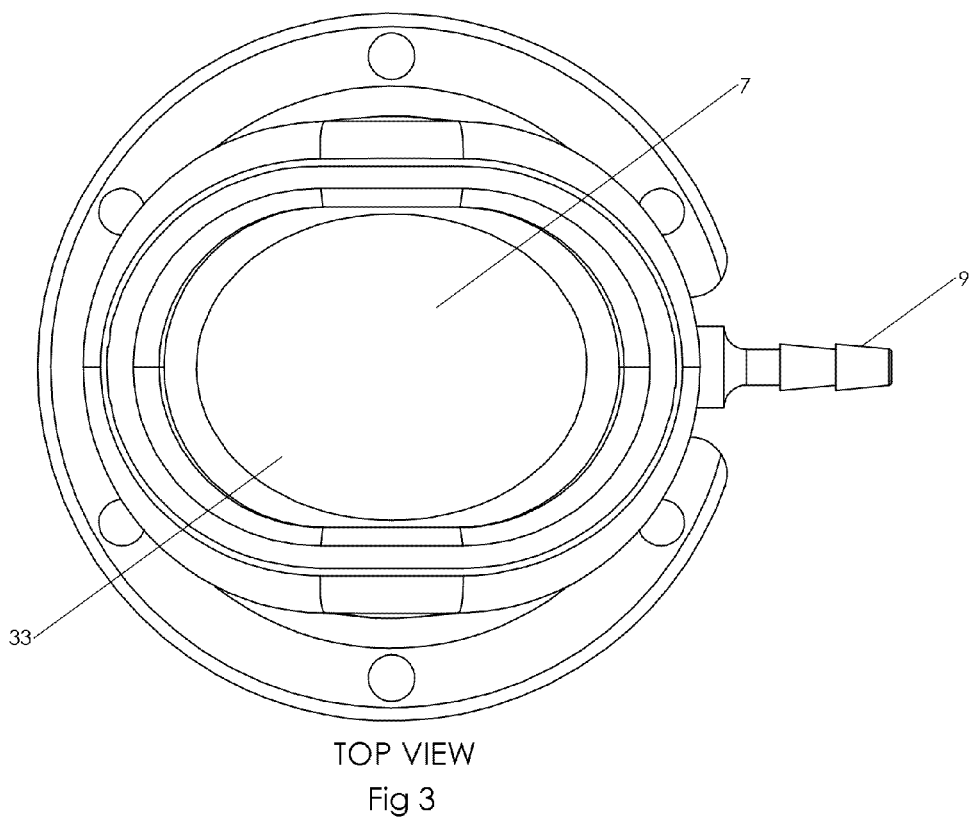
FIG. 3 is a top view of a spherical reservoir vascular access port designed in accordance with an embodiment of the present invention.
Figure 4:
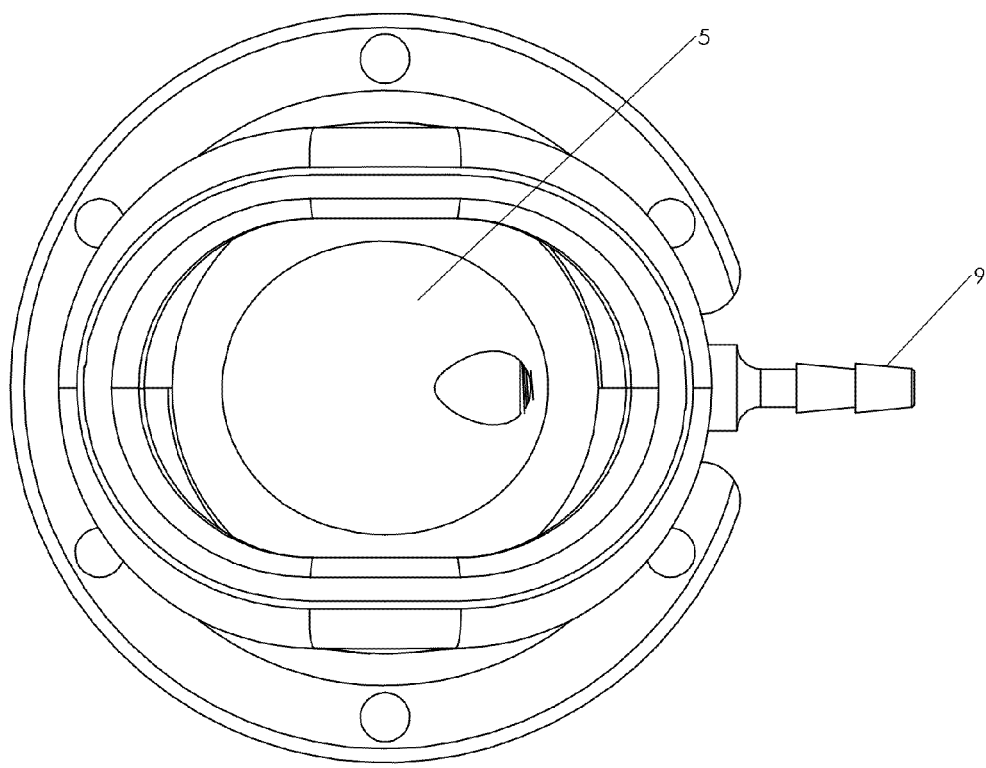
FIG. 4 is a top view of a spherical reservoir vascular access port with the septum removed designed in accordance with an embodiment of the present invention.
Figure 5:
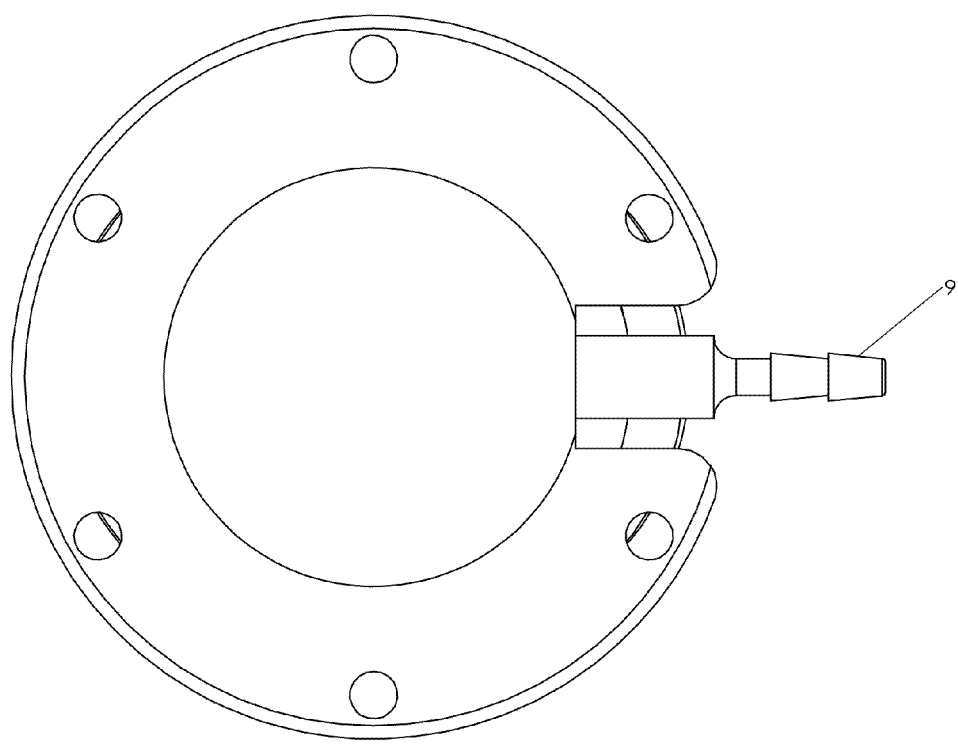
FIG. 5 is a bottom view of a spherical reservoir vascular access port designed in accordance with an embodiment of the present invention.
Figure 6:
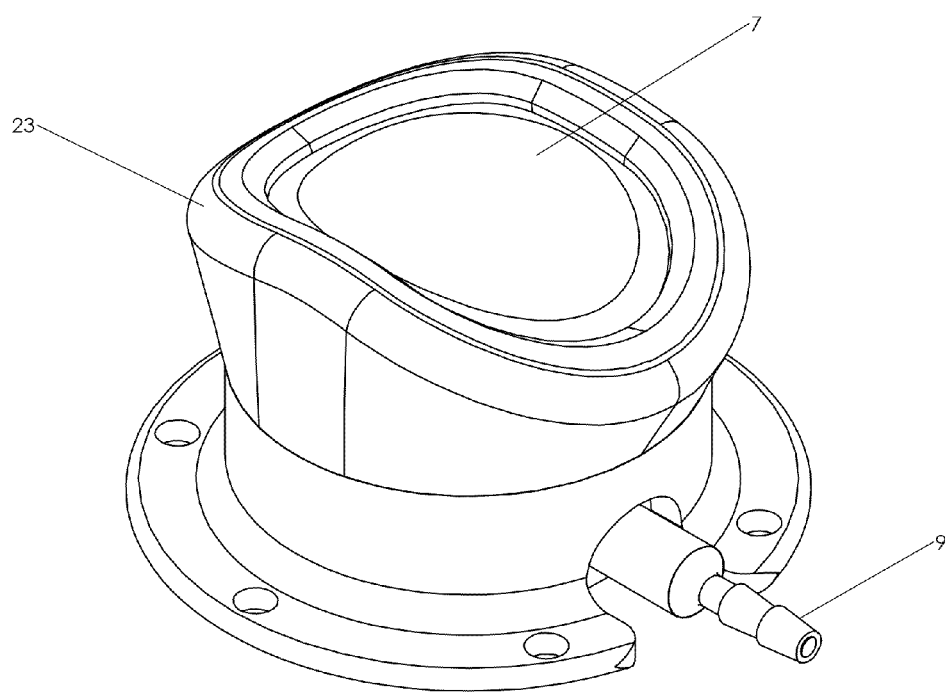
FIG. 6 is an isometric view of a spherical reservoir vascular access port designed in accordance with an embodiment of the present invention.

In a preferred embodiment, as illustrated in FIGS. 1a, 1b, 2a, 2b, 7a, 7b and 8, the non-planar, exterior surface of the septum 29 is radiused such that it is convex in shape and such that the center point 15 of the septum is in a higher plane than the perimeter 31 of the septum. As shown in FIG. 3, in one embodiment, the shape of the septum opening 33 may be elliptical in shape. The shape of the septum opening 33, however, may be of any conventional shape while maintaining the spherical nature of the reservoir, including, but not limited to, circular, elliptical, rectilinear, triangular, cross shaped, polygonal shaped, and star shaped.

Figure 25:
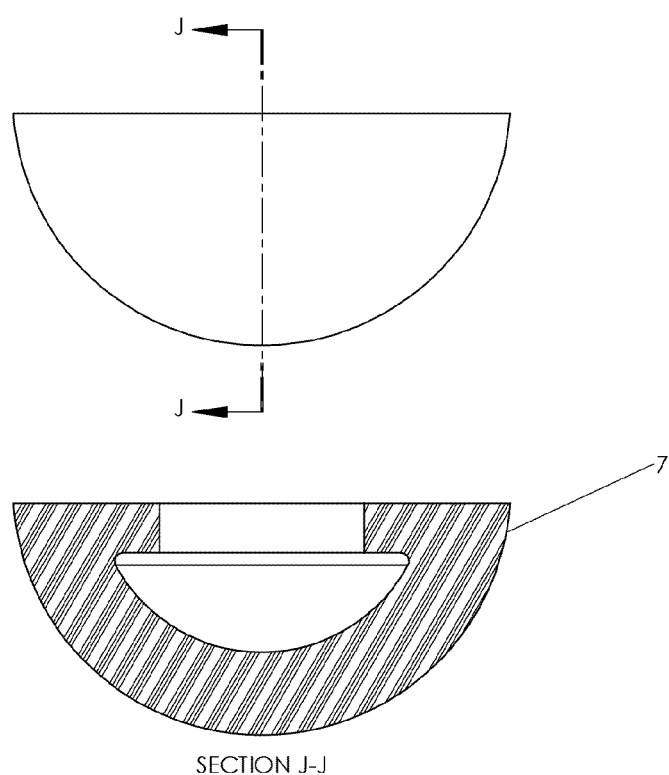
FIG. 25 is a cross sectional view of the septum of the present invention designed in accordance with an embodiment of the present invention.
Figure 26:
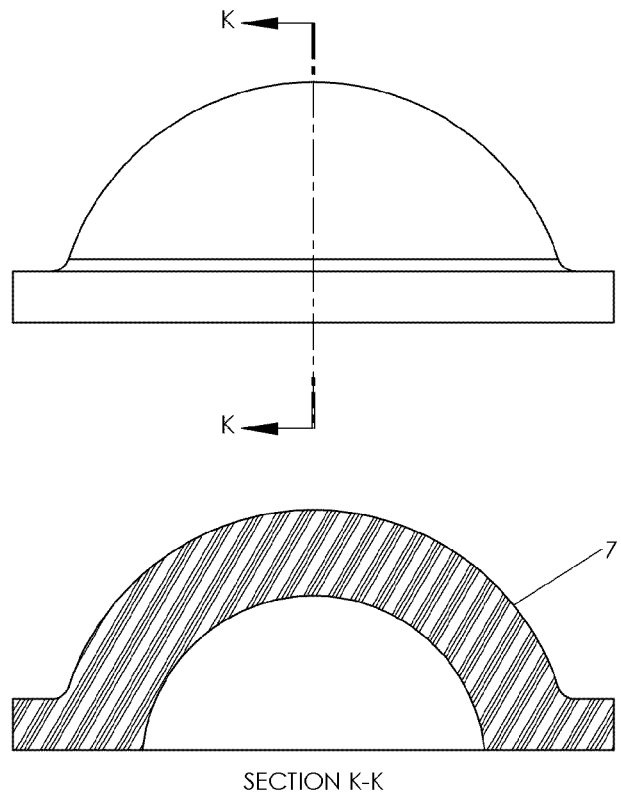
FIG. 26 is a cross sectional view of the septum of the present invention designed in accordance with an embodiment of the present invention wherein the septum is constructed to be self sealing and is inverted.

In another embodiment, the non-planar septum 7 may be constructed in a manner so that it is self-sealing. In such embodiment, as shown in FIGS. 25, 27a, and 28a, the non planar septum 7, prior to assembly, resembles a dome in shape. During the manufacture of the vascular access port, as shown in FIGS. 26, 27b and 28b, the dome is inverted, centered over the reservoir base and compressed. As shown in FIG. 28b, when the vascular access port is assembled, the inversion of dome creates an area of higher density at the top of the dome 35. Furthermore, the inversion of this area of increased density also provides a compressive force to the silicone material, thereby increasing the self-sealing capability of the port device.

Figure 9:
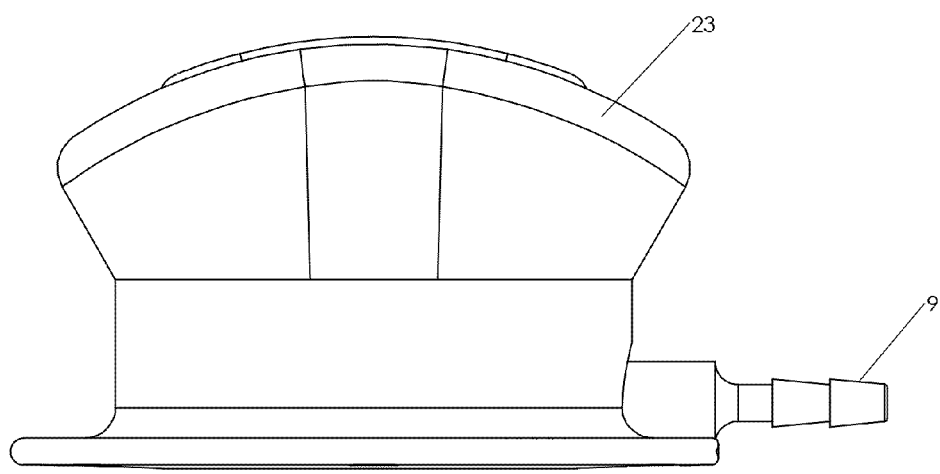
FIG. 9 is a front view of a spherical reservoir vascular access port designed in accordance with an embodiment of the present invention wherein the septum opening may be narrowed.
Figure 10:
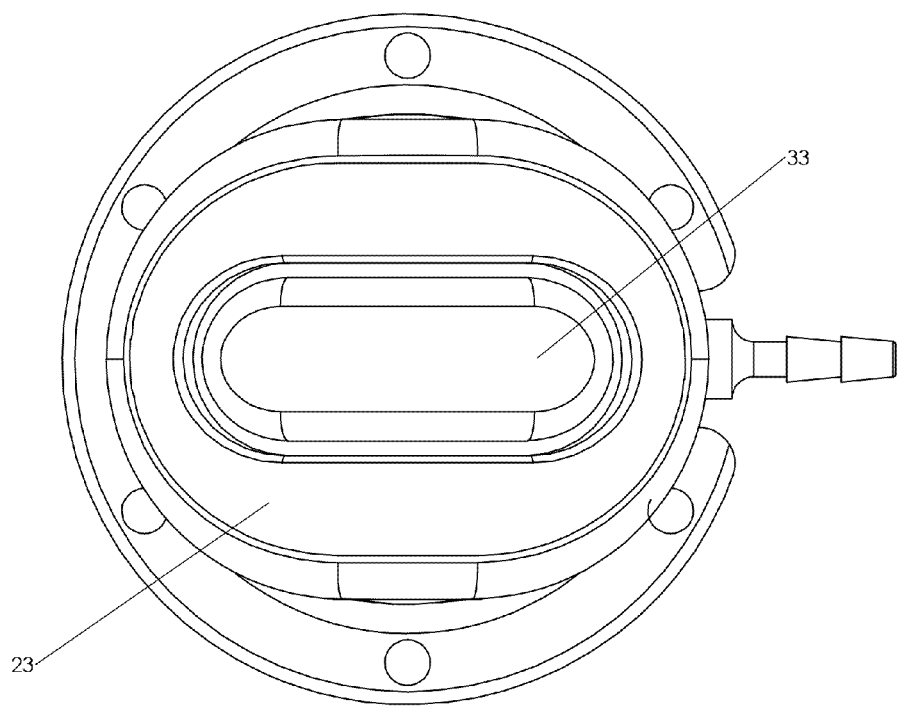
FIG. 10 is a top view of a spherical reservoir vascular access port designed in accordance with an embodiment of the present invention wherein the septum opening may be narrowed.
Figure 11:
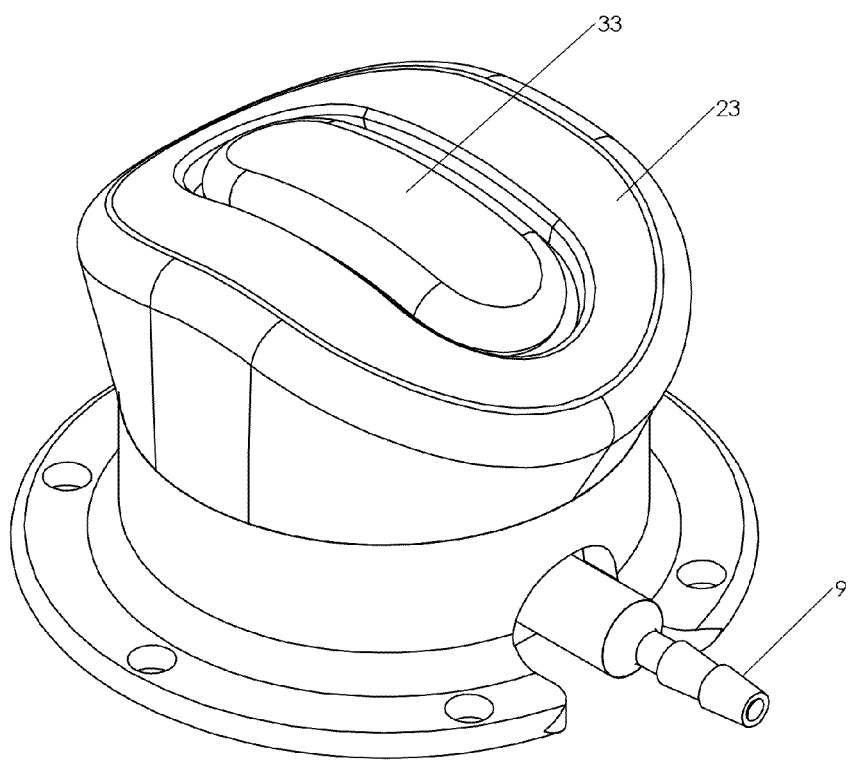
FIG. 11 is an isometric view of a spherical reservoir vascular access port designed in accordance with an embodiment of the present invention wherein the septum opening may be narrowed.
Figure 12:
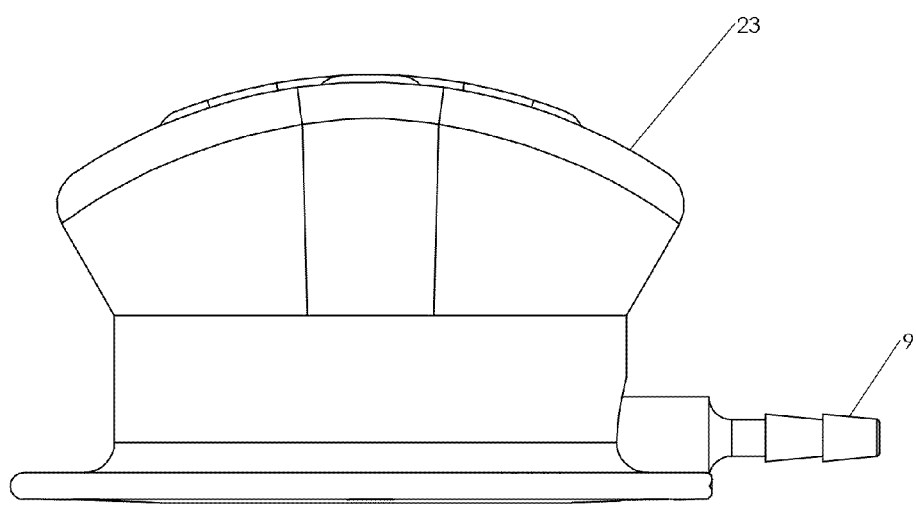
FIG. 12 is a front view of a spherical reservoir vascular access port designed in accordance with an embodiment of the present invention wherein the septum opening may be cross shaped.
Figure 13:
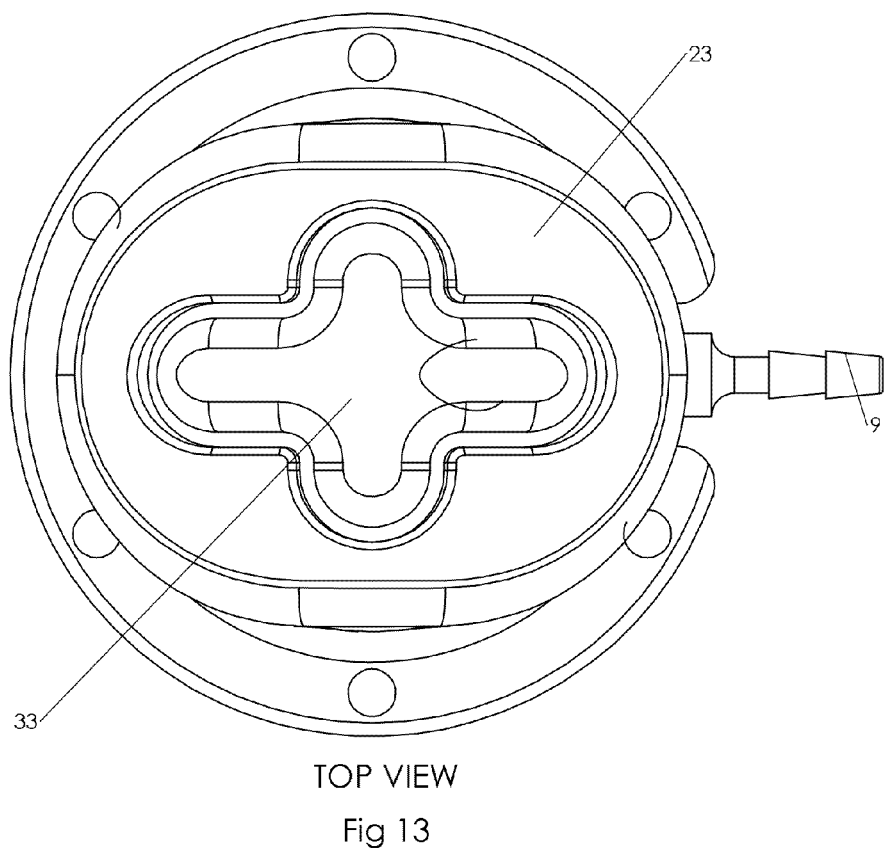
FIG. 13 is a top view of a spherical reservoir vascular access port designed in accordance with an embodiment of the present invention wherein the septum opening may be cross shaped.
Figure 14:
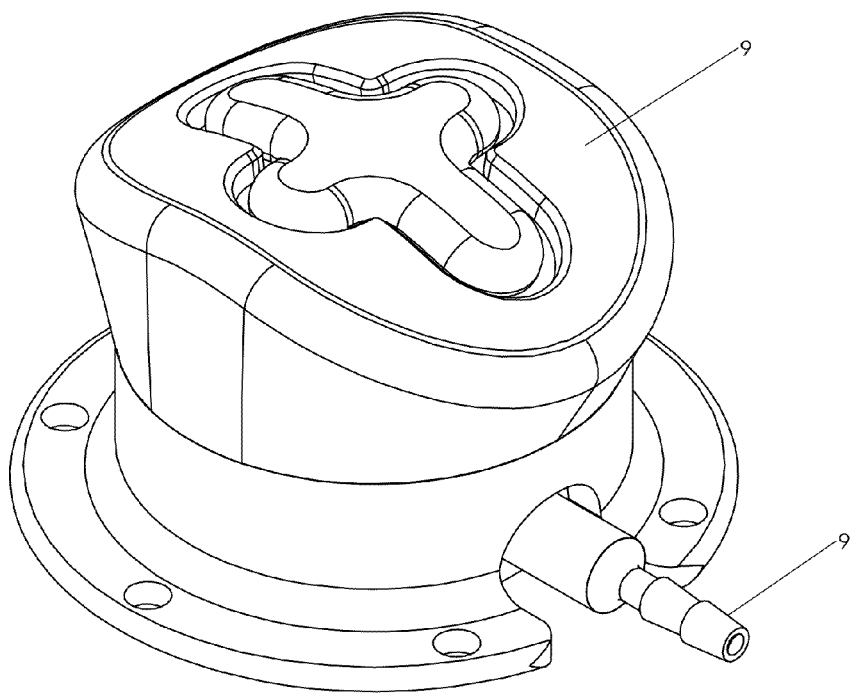
FIG. 14 is an isometric view of a spherical reservoir vascular access port designed in accordance with an embodiment of the present invention wherein the septum opening may be cross shaped.

As shown in FIGS. 9, 10, and 11, in one embodiment, the septum opening 33 may be a narrow elliptical shaped opening. The narrow elliptical opening provides the user with a smaller, narrower septum area. Alternatively, as shown in FIGS. 12, 13, and 14, the septum opening 33 may be cross shaped.

In one embodiment, as shown in FIG. 20, the septum opening 33 may be circular in shape as in standard vascular access ports. Since users already have a familiarity with circular shaped openings, the user will easily be able to palpate the septum area in this embodiment.

The convex or radiused shape of the septum 7 of the present invention further provides the benefit of always providing the user with the location of the high point 15 of the septum so that user always knows where to best access the port 1. Thus, the present invention also prevents the user from introducing the needle in the wrong location.

As shown in FIGS. 18b, and 19b, in one embodiment, the septum retainer ring may have a larger lip around the internal perimeter 35 of the septum retainer ring 23.

Figure 29:
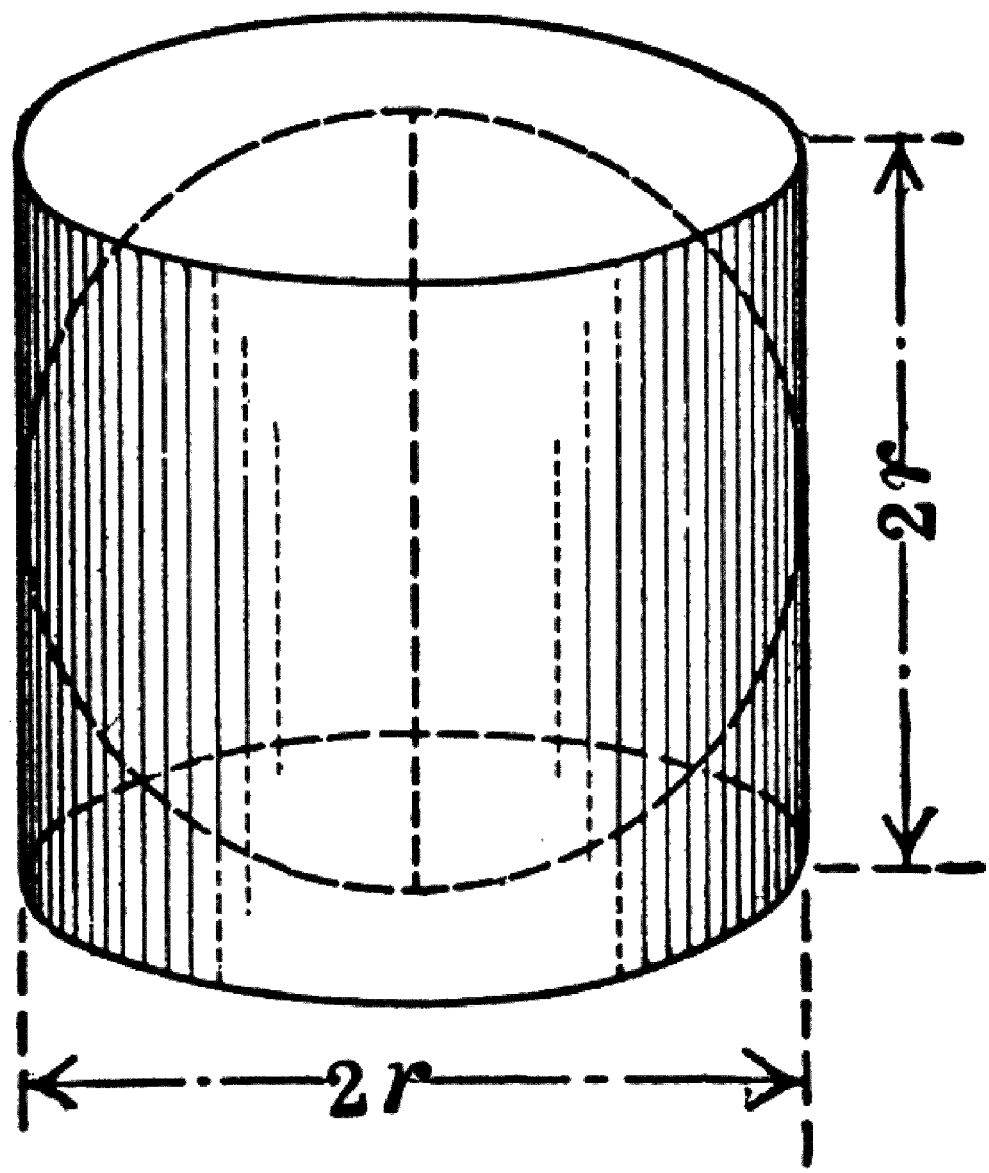
FIG. 29 is an illustration of the volume of a sphere relative to the volume of a cylinder.

The novel septum design and novel shape of the reservoir 5 of the present invention further has an impact on the volume of the reservoir. One of the significant purposes of the design of the present invention is the creation of an implantable vascular access port 1 with a smaller reservoir 5 and an easier flushing chamber. A standard vascular access port possesses a reservoir having a cylindrical shape which necessarily will have corners. The spherically shaped reservoir of the present invention provides for a smaller volume capacity when compared to standard cylindrical port designs. By eliminating angular junctions and providing smooth transitions between the bottom wall 27 of the reservoir and the continuous side wall 17, the volume of the reservoir 5 is decreased because the space offered by such corners is eliminated. The overall volume of the reservoir in a cylindrical port is determined by the diameter of the septum and the height of the reservoir. The height of the reservoir is determined by the length of the opening in the needle once it has been inserted into the septum. The opening of the needle is the distance between the point of the needle and the heel of the needle. The needle opening must pass through the septum such that the opening clears the septum to allow the infused fluid to flow into the attached catheter. The volume of a sphere is $4/3\ \pi R^3$ which is smaller than that of a comparable cylindrical reservoir port that is $\pi R^2 h$ where h is 2 R. As shown in FIG. 29, where a cylinder and sphere have the same radius and wherein the height of the cylinder is equal to the diameter of the sphere, the sphere will necessarily have a smaller volume. This is the mathematical comparison of a circumscribed cylinder to a sphere where R is essentially ½ of the diameter of the septum in a conventional port. Mathematically, the volume of the sphere is ⅔ the volume of a cylinder. In a cylindrically shaped reservoir port, therefore, a large septum diameter creates an extremely large volume, or dead space, in the reservoir due to the multiplication factor/squaring of the radius. The spherically shaped reservoir of the present invention, by definition, will necessarily have a smaller volume reservoir having the same "height" as a cylindrically shaped port.

One of the benefits of the present invention, therefore, is that a smaller volume reservoir is more efficient and easier to clean when compared to standard port designs. Further, one of the significant advantages of the present design is that the design provides for improved flushing and clearance characteristics while still maintaining the size, shape, and feel of a conventional port. The non-planar septum 7 of the present invention allows for a smaller volume reservoir 5 and precludes angular junctions present in standard ports that are difficult to flush clean. The spherical reservoir 5 of the present invention leads to less potential for partial cleaning and drug and blood residue accumulation in the reservoir. Partial cleaning and drug and blood residue accumulation may lead to infection, premature removal of the port, and/or significant costs of antibiotics.

The present invention, therefore, has been designed to decrease the reservoir volume, or "dead space", and is approximately 26% smaller than in a comparable standard port. The present invention has decreased the dead space from approximately 0.70 cc in a comparable standard port to approximately 0.48 cc in the present design. On its face, the change of only 0.22 cc may not seem significant; however, it is quite significant when considering that a full flush generally utilizes 10 cc's of fluid. Such a decrease in dead space means that the turn over of fluid in the dead space increases from 13 times to 18 times, which can be considered a significant change and a significantly improved safety margin.

In a study conducted by the Applicant, the present invention was tested against standard ports currently sold on the market to determine the flushing ability of the present invention. The flushing abilities of the ports were measured by testing the change in conductivity between two solutions of differing conductivity, a filling solution and a flushing solution, to determine the clearance volume, or exchange of fluids. To measure the conductivity of both of these solutions, and therefore, accurately monitor the conductivity change that occurs when the flushing solution replaces the filling solution, a conductivity cell/meter attached to the end of the catheter was used. Prior to testing, both solutions conductivity was measured.

Before testing began, all parts were conditioned in the water bath at 37° C.±2° C. A port was then connected to the conductivity cell via the catheter, filled with the filling solution, and allowed to equilibrate. It is important to note that the inner diameters for all catheter and lengths were the same, thereby nullifying the effect of the catheter dead space. Next, a reading was taken from the conductivity meter and recorded as the 'Start Conductivity'. A 20 Ga non-coring needle set was then attached to a 60 mL syringe filled with flushing solution and mounted on a syringe pump. The needle set was purged/primed and then used to puncture the port septum at an orientation of 0°. The syringe pump was set to a constant flow rate (5, 10, or 20 mL/min) and allowed to deliver the flushing solution into the port until the conductivity meter read the measured conductivity of the flushing solution. This was recorded as the 'End Conductivity'. The total volume of flushing solution pumped was recorded as the 'Clearance Volume'. System filling and flushing were repeated 5 times for each port and flow rate.

Data from the study confirms the hypothesis that the improvements offered by the present invention result in a clearance volume less than that of standard ports in the market. Further, standard ports required a higher flow rate of flushing solution to decrease the average clearance volume. In the case of the present invention, the data suggests that its clearance volume is independent of flow rate. That is, regardless of the flow rate, the present invention will clear with the same volume of flushing solution. This sets it apart from the other ports, which, according to the data, are dependent upon flow rate to reduce their clearance volumes. As such, the design of the present invention adds another level of safety to the flushing of the port, as hand-delivered flow rates in the field are most certainly variable.

Flushing parameters and protocols vary based on port size and manufacturer; however, typical recommended flushing volumes range from 10-20 mL. Based on the findings in the study, and using the highest average value obtained for the present invention, 2.44 mL, the present invention provides for a safety factor of 4.1-8.2, which is certainly higher than that of the other ports analyzed in the study.

Moreover, because the data suggests that the present invention's clearance volume is independent of flow rate, a minimum hand-delivered flow rate does not have to be assumed to ensure port clearance.

Figure 30:
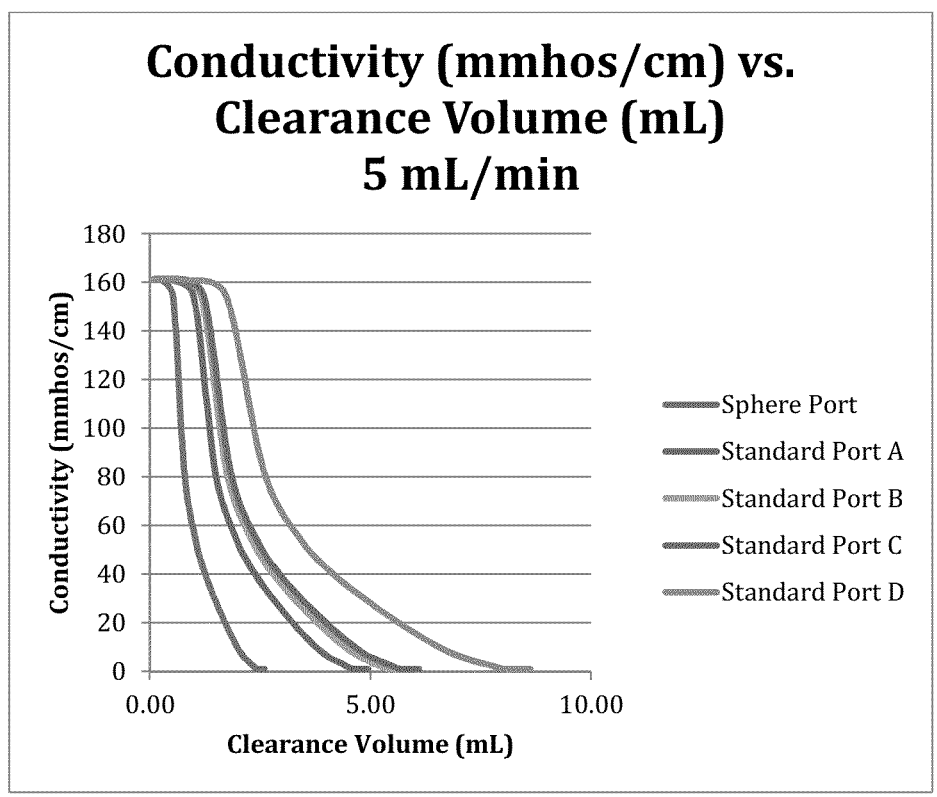
FIG. 30 is a chart illustrating the conductivity of ports tested against the clearance volume at a rate of 5 mL/min.
Figure 31:
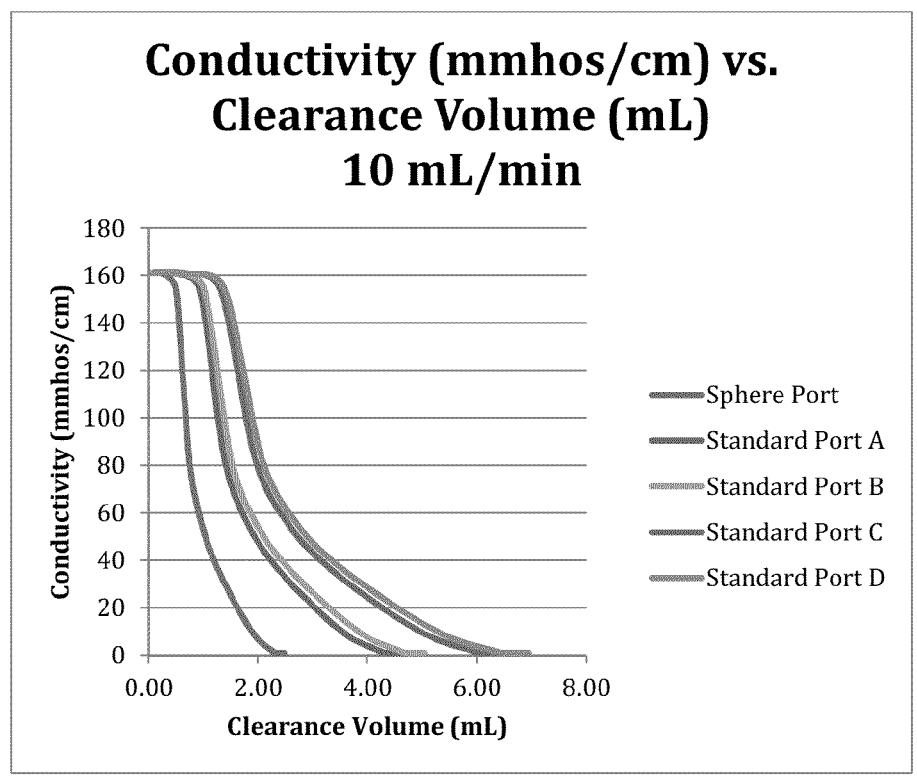
FIG. 31 is a chart illustrating the conductivity of ports tested against the clearance volume at a rate of 10 mL/min.
Figure 32:
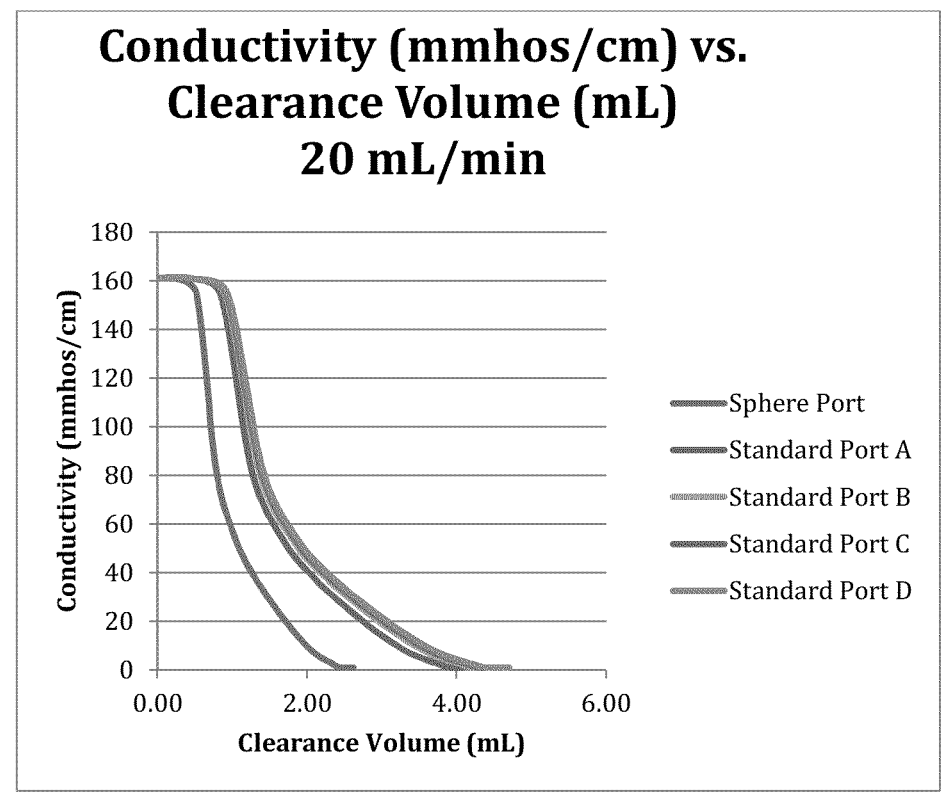
FIG. 32 is a chart illustrating the conductivity of ports tested against the clearance volume at a rate of 20 mL/min.

Charts 1, 2, and 3 (FIGS. 30, 31 and 32), detail the dilution curves for each port with respect to the flow rates tested. Although the charts graph conductivity vs. clearance volume, clearance time could be substituted for clearance volume. The present invention showed the steepest dilution curve. In general, as flow rate increased, the dilution curves became more similar.

Figures 15A, 15B:
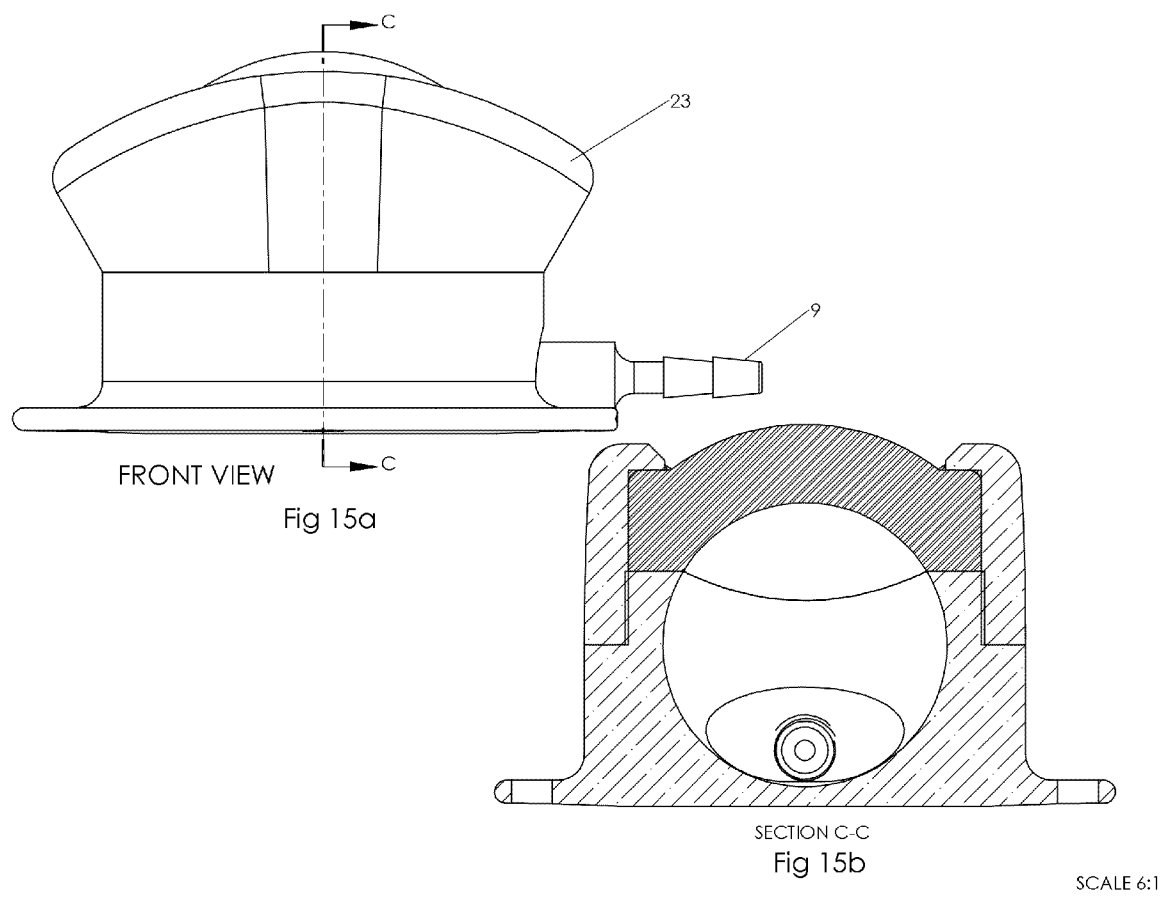
FIG. 15a is a front view of a spherical reservoir vascular access port designed in accordance with an embodiment of the present invention wherein the reservoir forms a funnel leading to the outlet means.
FIG. 15b is a cross sectional view of a spherical reservoir vascular access port designed in accordance with an embodiment of the present invention wherein the reservoir forms a funnel leading to the outlet means.
Figures 16A, 16B:
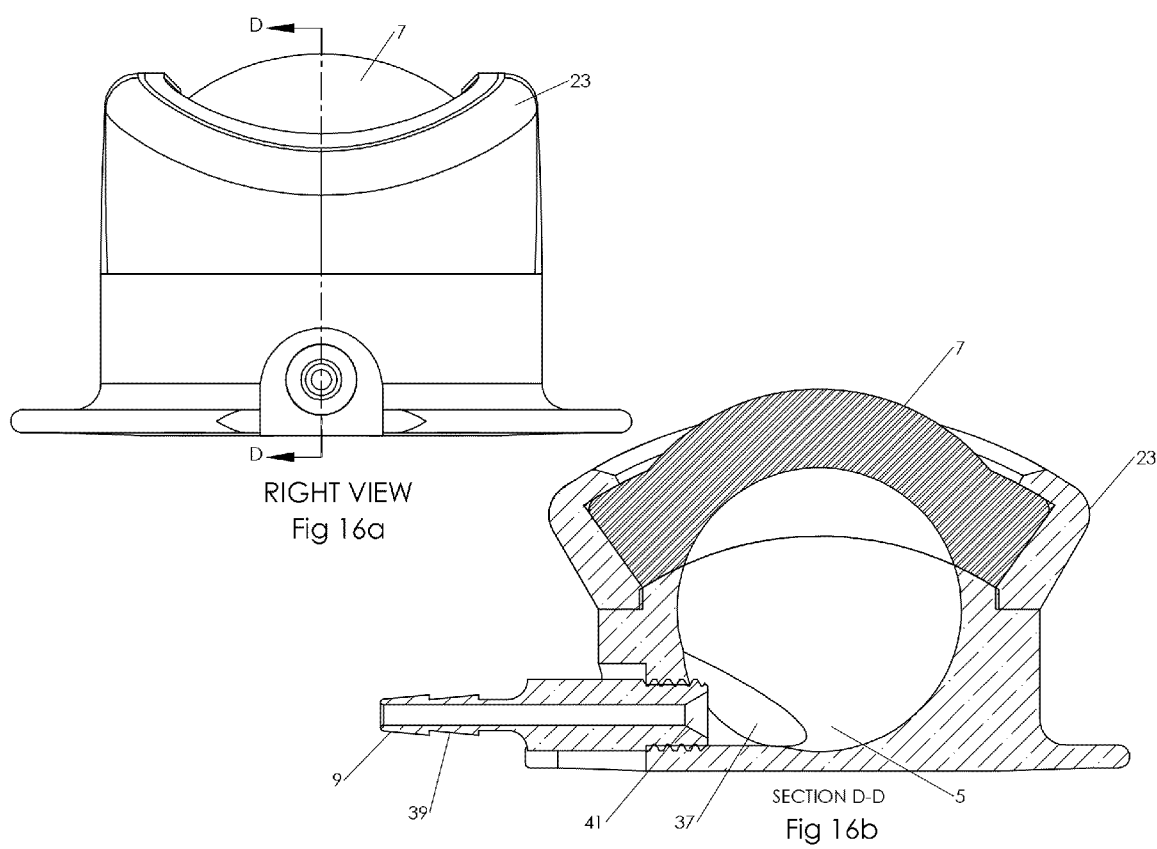
FIG. 16a is a side right view of a spherical reservoir vascular access port designed in accordance with an embodiment of the present invention wherein the reservoir forms a funnel leading to the outlet means.
FIG. 16b is a cross sectional view of a spherical reservoir vascular access port designed in accordance with an embodiment of the present invention wherein the reservoir forms a funnel leading to the outlet means.

As shown in FIGS. 1a, 1b, 2a, and 2b, to further increase the flushing efficiency, the outlet means 9 of the present invention may be directed along the plane of the bottom wall 27 of the reservoir 5 to create a more efficient flow pattern. Unlike the prior art, wherein the outlet means intersect the reservoir at a height approximately midway between the bottom wall of the reservoir and the septum, the present invention allows the fluid being flushed to flow smoothly from the bottom of the reservoir 13 through the outlet means 9. As shown in FIGS. 15b and 16b to further improve the flow pattern, the structure 37 surrounding the outlet opening may be beveled, chamfered, or rounded to form a funnel to improve the flow of fluids from the reservoir 5 to the outlet tube 39. The beveled, chamfered, or rounded area 37 leading to the outlet opening provides a more efficient flow pattern from the reservoir 5 to the outlet tube 39. The novel design of the reservoir 5 permits efficient cleaning of the reservoir 5 and other components of the infusion port 1.

Figure 17:
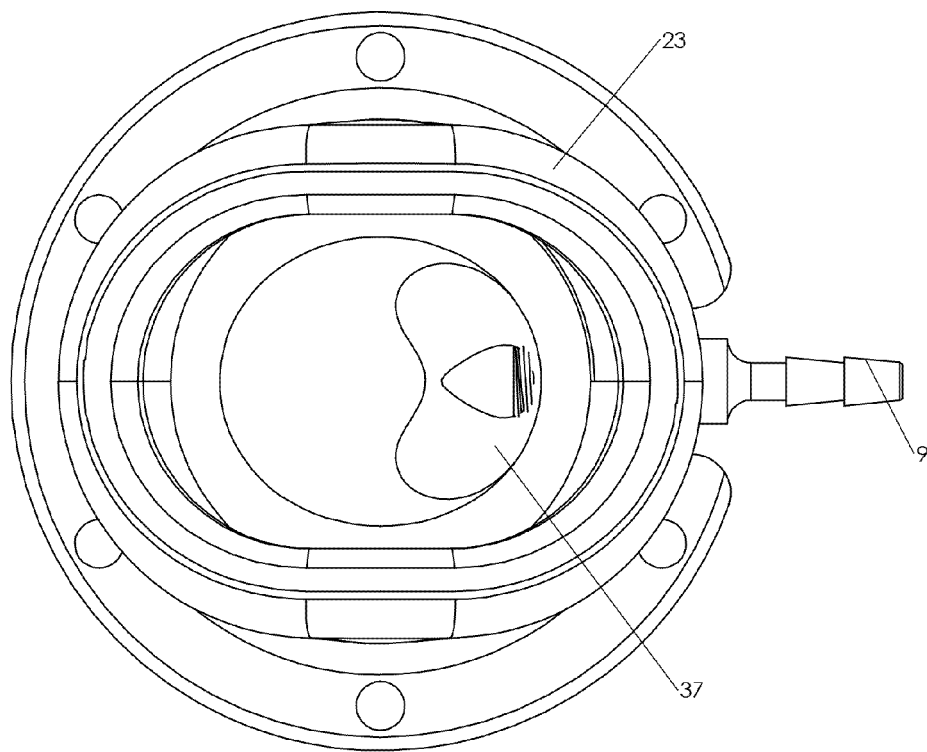
FIG. 17 is a top view of a spherical reservoir vascular access port with the septum removed designed in accordance with an embodiment of the present invention.
Figure 21A:
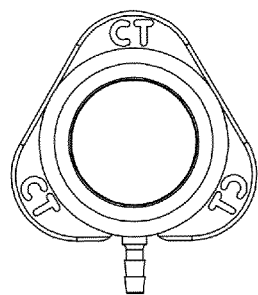
FIG. 21a is a top view of a spherical reservoir vascular access port designed in accordance with an embodiment of the present invention wherein the suture holes are combination of suture holes and cut outs of the letters "CT"
Figure 21B:
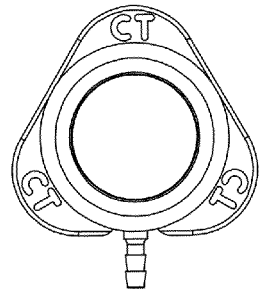
FIG. 21b is a top view of a spherical reservoir vascular access port designed in accordance with an embodiment of the present invention wherein the suture holes are combination of suture holes and cut outs of the letters "CT"
Figure 21C:
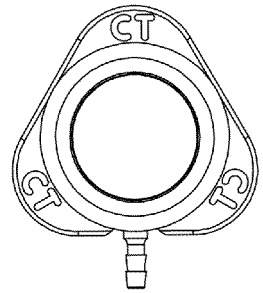
FIG. 21c a top view of a spherical reservoir vascular access port designed in accordance with an embodiment of the present invention.
Figure 23:
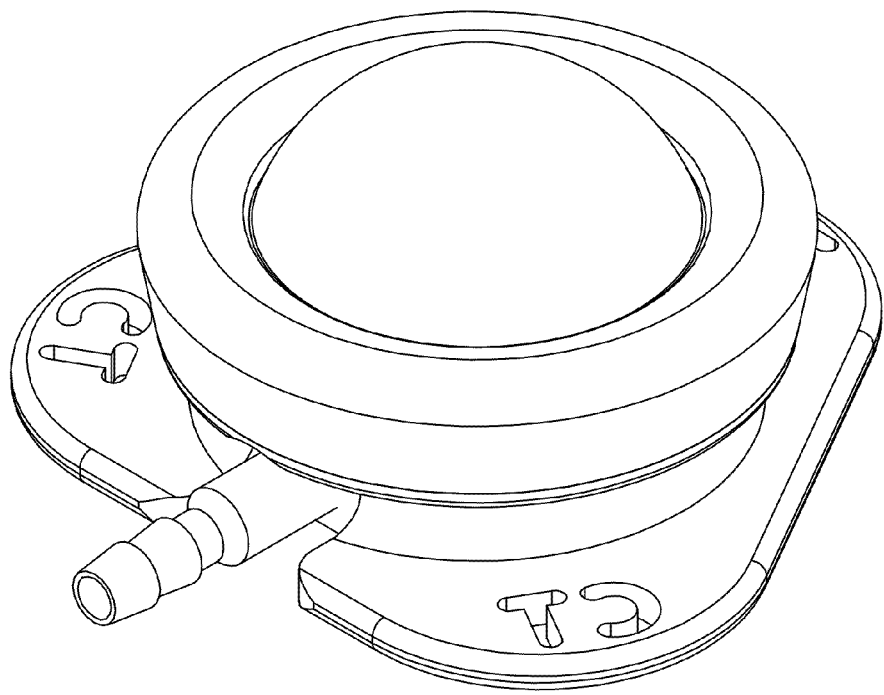
FIG. 23 is an isometric view of a spherical reservoir vascular access port designed in accordance with an embodiment of the present invention wherein the suture holes are combination of suture holes and cut outs of the letters "CT"
Figure 24:
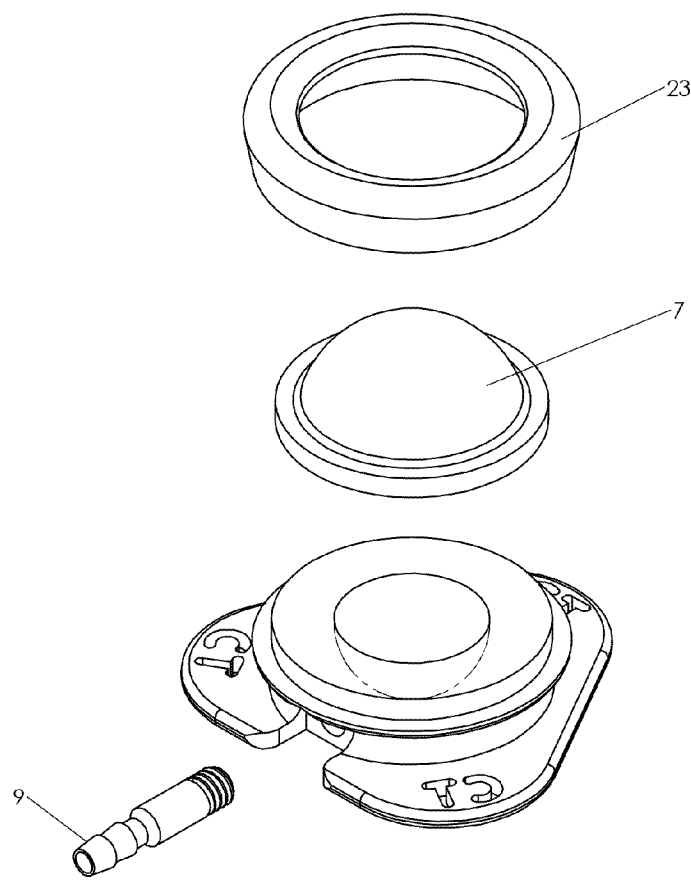
FIG. 24 is an exploded isometric view of a spherical reservoir vascular access port designed in accordance with an embodiment of the present invention wherein the suture holes are combination of suture holes and cut outs of the letters "CT"

In a preferred embodiment, as shown in FIGS. 15b, 16b and 17, the area 37 of the reservoir leading to, and surrounding, the outlet opening 41 may form a funnel 37 leading to the outlet means 9 of the present invention to create a more efficient flow pattern. The funnel 37 leading to the outlet opening 41 allows the fluid being flushed to flow smoothly from the bottom of the reservoir 13 through the outlet means 9. The funnel 37 enhances the smooth flow of material and fluids into and out of the reservoir 5. The outlet 9, as shown in FIGS. 15b and 16b, can be partially recessed, i.e., partially defined or formed within the floor 27 of the reservoir to act like a drain to remove fluid and particles from the reservoir 5.

Although the description above contains much specificity, these should not be construed as limiting the scope of the invention but as merely providing illustrations of some of the presently preferred embodiments of this invention.

We hereby claim:

1. An improved vascular access port comprising: a) a rigid reservoir base having a partial hemispherical interior bottom surface; b) outlet means; and c) an elastomeric, needle penetrable, non-planar septum wherein the interior of the septum is partially hemispherical such that when the septum seals to the reservoir base forms a spherically shaped reservoir.

2. An improved vascular access port according to claim 1, wherein the septum is radiused.

3. An improved vascular access port according to claim 1, wherein the reservoir base leading to the outlet means is chamfered.

4. An improved vascular access port according to claim 1, wherein the reservoir base forms a funnel outlet leading to the outlet means.

5. An improved vascular access port according to claim 1, wherein the outlet means are directed along the plane of the bottom wall of the reservoir.

6. An improved vascular access port according to claim 1, wherein the reservoir base forms a septum opening which is an elongated elliptical shaped opening.

7. An improved vascular access port according to claim 1, wherein the reservoir base forms a septum opening which is a star shaped opening.

8. An improved vascular access port according to claim 1, wherein the reservoir base forms a septum opening which is a cross shaped opening.

9. An improved vascular access port according to claim 1, wherein the reservoir base forms a septum opening which is elongated.

10. An improved vascular access port comprising: a) a rigid reservoir base having a partial hemispherical interior bottom surface; b) outlet means; and c) an elastomeric, needle penetrable, non-planar septum wherein the exterior of the septum is convex and the interior of the septum is partially hemispherical such that when the septum seals to the reservoir base forms a semi-spherically shaped reservoir.

11. An improved vascular access port according to claim 10, wherein the septum is radiused.

12. An improved vascular access port according to claim 10, wherein the reservoir base leading to the outlet means is chamfered.

13. An improved vascular access port according to claim 10, wherein the reservoir base forms a funnel outlet leading to the outlet means.

14. An improved vascular access port according to claim 10, wherein the outlet means are directed along the plane of the bottom wall of the reservoir.

15. An improved vascular access port according to claim 10, wherein the reservoir base forms a septum opening which is an elongated elliptical shaped opening.

16. An improved vascular access port according to claim 10, wherein the reservoir base forms a septum opening which is a star shaped opening.

17. An improved vascular access port according to claim 10, wherein the reservoir base forms a septum opening which is a cross shaped opening.

18. An improved vascular access port according to claim 10, wherein the reservoir base forms a septum opening which is elongated.

19. An improved vascular access port comprising: a) a rigid reservoir base having a partially hemispherical interior bottom surface; b) outlet means; and c) an elastomeric, needle penetrable, non-planar septum that is partially hemispherical that when assembled to the reservoir base forms a substantially spherical interior surface in the top portion of the reservoir.

20. An improved vascular access port according to claim 19, wherein the septum is radiused.

21. An improved vascular access port according to claim 19, wherein the reservoir base leading to the outlet means is chamfered.

22. An improved vascular access port according to claim 19, wherein the reservoir base forms a funnel outlet leading to the outlet means.

23. An improved vascular access port according to claim 19, wherein the outlet means are directed along the plane of the bottom wall of the reservoir.

24. An improved vascular access port according to claim 19, wherein the reservoir base forms a septum opening which is an elongated elliptical shaped opening.

25. An improved vascular access port according to claim 19, wherein the reservoir base forms a septum opening which is a star shaped opening.

26. An improved vascular access port according to claim 19, wherein the reservoir base forms a septum opening which is elongated.

27. An improved vascular access port according to claim 19, wherein the reservoir base forms a septum opening which is a cross shaped opening.

28. An improved vascular access port comprising: a) a rigid reservoir base having a substantially hemispherical interior bottom surface; b) outlet means; and c) an elastomeric, needle penetrable, non-planar septum that is substantially hemispherical that when assembled to the reservoir base forms a substantially spherically shaped reservoir.

29. An improved vascular access port according to claim 28, wherein the septum is radiused.

30. An improved vascular access port according to claim 28, wherein the reservoir base leading to the outlet means is chamfered.

31. An improved vascular access port according to claim 28, wherein the reservoir base forms a funnel outlet leading to the outlet means.

32. An improved vascular access port according to claim 28, wherein the outlet means are directed along the plane of the bottom wall of the reservoir.

33. An improved vascular access port according to claim 28, wherein the septum opening is an elongated elliptical shaped opening.

34. An improved vascular access port according to claim 28, wherein the septum opening is a star shaped opening.

35. An improved vascular access port according to claim 28, wherein the septum opening is a cross shaped opening.

36. An improved vascular access port according to claim 28, wherein the septum opening is elongated.

37. An improved vascular access port comprising: a) a rigid reservoir base having a partial hemispherical interior bottom surface; b) outlet means; and c) an elastomeric, needle penetrable, non-planar septum that is partially hemispherical that when assembled to the reservoir base forms a spherically shaped reservoir, wherein said reservoir provides for the improved vascular access port to have a clearance volume independent of flow rate.

38. An improved vascular access port according to claim 37, wherein the reservoir base forms a funnel outlet leading to the outlet means.

39. An improved vascular access port according to claim 37, wherein the outlet means are directed along the plane of the bottom wall of the reservoir.

40. An improved vascular access port according to claim 37, wherein the reservoir base forms a septum opening which is an elongated elliptical shaped opening.

41. An improved vascular access port according to claim 37, wherein the reservoir base forms a septum opening which is a star shaped opening.

42. An improved vascular access port according to claim 37, wherein the reservoir base forms a septum opening which is a cross shaped opening.

43. An improved vascular access port according to claim 37, wherein the reservoir base forms a septum opening which is elongated.

44. An improved vascular access port comprising: g) a rigid reservoir base having a partial hemispherical interior bottom surface wherein the portion of the reservoir base leading to the outlet means is rounded; h) outlet means; and i) an elastomeric, needle penetrable, non-planar septum that is partially hemispherical that when assembled to the reservoir base forms a spherically shaped reservoir.

45. An improved vascular access port according to claim 44, wherein the reservoir base forms a funnel outlet leading to the outlet means.

46. An improved vascular access port according to claim 44, wherein the outlet means are directed along the plane of the bottom wall of the reservoir.

* * * * *